US012714301B2

(12) United States Patent
Nakamura et al.

(10) Patent No.: US 12,714,301 B2
(45) Date of Patent: Aug. 25, 2026

(54) VISUAL FIELD TESTING METHOD, VISUAL FIELD TESTING DEVICE, AND VISUAL FIELD TESTING PROGRAM

(71) Applicant: NIKON CORPORATION, Tokyo (JP)

(72) Inventors: Chikara Nakamura, Tokyo (JP); Taishi Aoki, Narashino (JP); Teruo Horikawa, Inagi (JP); Hisao Osawa, Kashiwa (JP)

(73) Assignee: NIKON CORPORATION, Tokyo (JP)

( * ) Notice: Subject to any disclaimer, the term of this patent is extended or adjusted under 35 U.S.C. 154(b) by 262 days.

(21) Appl. No.: 18/538,297

(22) Filed: Dec. 13, 2023

(65) Prior Publication Data

US 2024/0122465 A1 Apr. 18, 2024

Related U.S. Application Data

(63) Continuation of application No. PCT/JP2022/023856, filed on Jun. 14, 2022.

(30) Foreign Application Priority Data

Jun. 16, 2021 (JP) ................................. 2021-100268

(51) Int. Cl.
*A61B 3/024* (2006.01)

(52) U.S. Cl.
CPC .................................. *A61B 3/024* (2013.01)

(58) Field of Classification Search
CPC ............ A61B 3/02; A61B 3/022; A61B 3/028
(Continued)

(56) References Cited

U.S. PATENT DOCUMENTS 6,527,391 B1 * 3/2003 Heijl ...................... A61B 3/024 351/243
8,425,039 B2 * 4/2013 Gonzalez de la Rosa ................. A61B 3/024 351/224

(Continued)

FOREIGN PATENT DOCUMENTS

JP 2008-036297 A 2/2008
JP 5048284 B2 10/2012
JP 2014-166250 A 9/2014

OTHER PUBLICATIONS

Yamamoto, Tetsuya, and Tanihara, Hidenobu, All about Open-Angle Glaucoma. 1st Edition, 1st Printing, Apr. 1, 2013, pp. 218-220, ISBN978-4-260-01766-4, (Igaku-Shoin Ltd.), non-official translation (Yamamoto, Tetsuya, Tanihara, Hidenobu, All about Open-Angle Glaucoma. 1st Edition, 1st Printing; partial translation of p. 218, lines 2-5; p. 219, lines 16-17; p. 220, fig. 6 (5 pages).

(Continued)

*Primary Examiner* — Marin Pichler
(74) *Attorney, Agent, or Firm* — Foley & Lardner LLP

(57) ABSTRACT

A visual field testing method is a visual field testing method of testing a visual field range divided into at least a first partial area and a second partial area, the method including: a step of measuring sensitivities of a plural first test points that are included in the first partial area; and a step of performing a process of estimating sensitivities of a plural second test points that are included in the first partial area and are test points other than the first test points, by using the sensitivities of the plural first test points.

21 Claims, 53 Drawing Sheets

(58) Field of Classification Search
USPC ................................ 351/224, 222, 225, 226
See application file for complete search history.

(56) References Cited

U.S. PATENT DOCUMENTS

| | | | | |
|---|---|---|---|---|
| 2004/0057013 | A1* | 3/2004 | Cappo .................... | A61B 3/024 351/224 |
| 2008/0036965 | A1 | 2/2008 | Shimada | |
| 2015/0201828 | A1* | 7/2015 | Hara .................... | A61B 3/0025 351/246 |
| 2016/0015263 | A1 | 1/2016 | Asaoka et al. | |

OTHER PUBLICATIONS

International Search Report and Written Opinion of the International Searching Authority issued in the corresponding International Patent Application No. PCT/JP2022/023856, dated Aug. 9, 2022 (11 pages).
Japanese Office Action and translation issued in JP Application No. 2025-018738 dated Jan. 27, 2026 (6 pages).

* cited by examiner

FIG.2

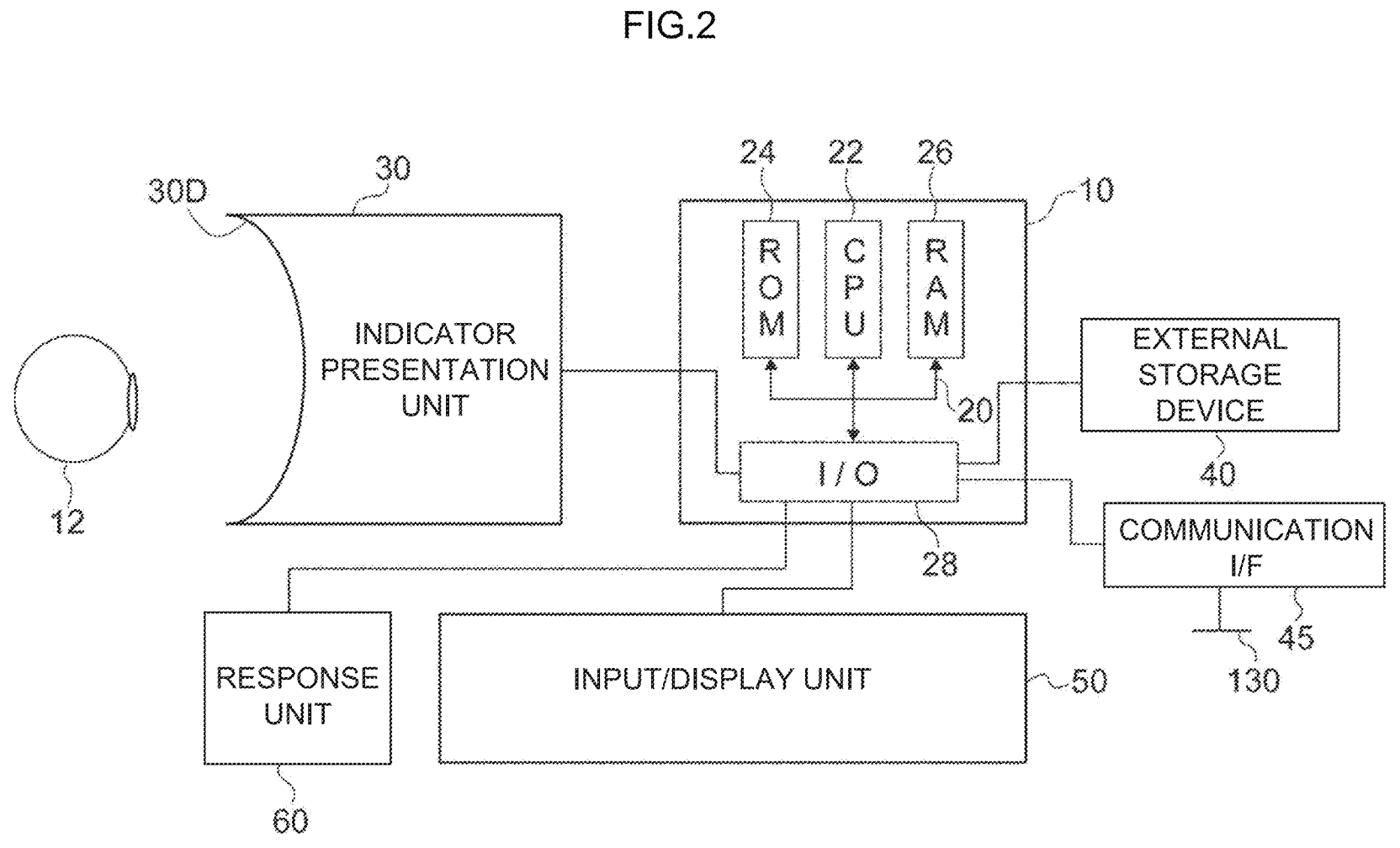

EXTERNAL STORAGE DEVICE
40
COMMUNICATION I/F
45
130
10
RAM
26
CPU
22
ROM
24
20
I/O
28
50
INPUT/DISPLAY UNIT
INDICATOR PRESENTATION UNIT
30
30D
RESPONSE UNIT
60
12

⬠: ADDITIONAL TEST POINT

: ADDITIONAL TEST POINT

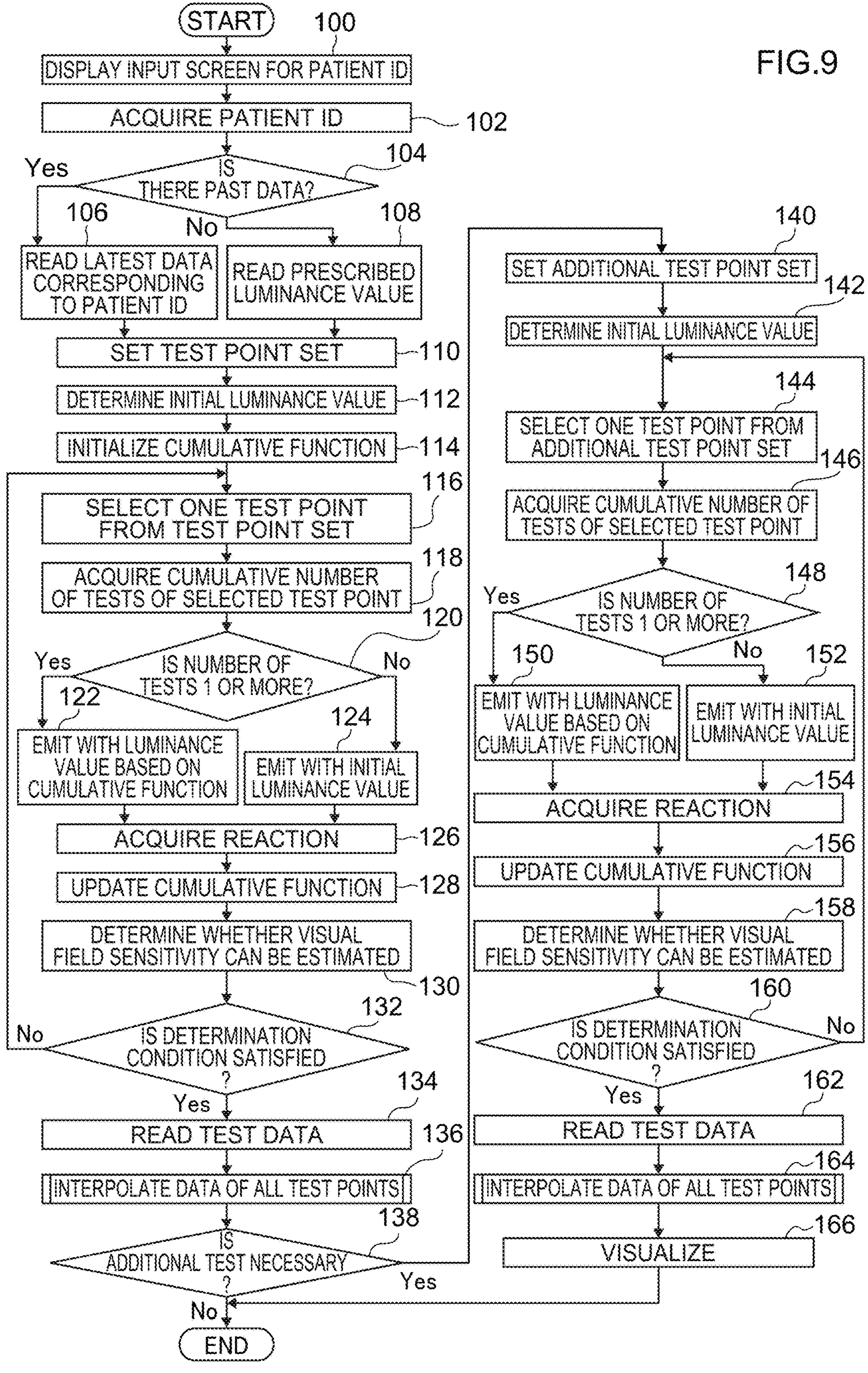
FIG.9
START
100
DISPLAY INPUT SCREEN FOR PATIENT ID
ACQUIRE PATIENT ID
102
IS THERE PAST DATA?
104
Yes
No
106
READ LATEST DATA CORRESPONDING TO PATIENT ID
108
READ PRESCRIBED LUMINANCE VALUE
SET TEST POINT SET
110
DETERMINE INITIAL LUMINANCE VALUE
112
INITIALIZE CUMULATIVE FUNCTION
114
SELECT ONE TEST POINT FROM TEST POINT SET
116
ACQUIRE CUMULATIVE NUMBER OF TESTS OF SELECTED TEST POINT
118
IS NUMBER OF TESTS 1 OR MORE?
120
Yes
No
122
EMIT WITH LUMINANCE VALUE BASED ON CUMULATIVE FUNCTION
124
EMIT WITH INITIAL LUMINANCE VALUE
ACQUIRE REACTION
126
UPDATE CUMULATIVE FUNCTION
128
DETERMINE WHETHER VISUAL FIELD SENSITIVITY CAN BE ESTIMATED
130
IS DETERMINATION CONDITION SATISFIED ?
132
No
Yes
READ TEST DATA
134
INTERPOLATE DATA OF ALL TEST POINTS
136
IS ADDITIONAL TEST NECESSARY ?
138
Yes
No
END
140
SET ADDITIONAL TEST POINT SET
142
DETERMINE INITIAL LUMINANCE VALUE
144
SELECT ONE TEST POINT FROM ADDITIONAL TEST POINT SET
146
ACQUIRE CUMULATIVE NUMBER OF TESTS OF SELECTED TEST POINT
148
IS NUMBER OF TESTS 1 OR MORE?
Yes
No
150
EMIT WITH LUMINANCE VALUE BASED ON CUMULATIVE FUNCTION
152
EMIT WITH INITIAL LUMINANCE VALUE
154
ACQUIRE REACTION
156
UPDATE CUMULATIVE FUNCTION
158
DETERMINE WHETHER VISUAL FIELD SENSITIVITY CAN BE ESTIMATED
160
IS DETERMINATION CONDITION SATISFIED ?
No
Yes
162
READ TEST DATA
164
INTERPOLATE DATA OF ALL TEST POINTS
166
VISUALIZE FIG.14C
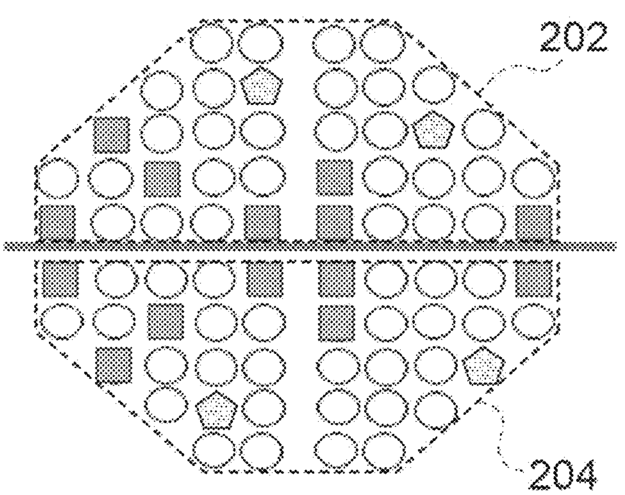

▲ : VISUAL FIELD SENSITIVITY DEFECTIVE POINT

▲: VISUAL FIELD SENSITIVITY DEFECTIVE POINT

⬠: ADDITIONAL TEST POINT

▲ : VISUAL FIELD SENSITIVITY DEFECTIVE POINT

▲: VISUAL FIELD SENSITIVITY DEFECTIVE POINT

⬠: ADDITIONAL TEST POINT

▲ : VISUAL FIELD SENSITIVITY DEFECTIVE POINT

▲ : VISUAL FIELD SENSITIVITY DEFECTIVE POINT

⬠ : ADDITIONAL TEST POINT

FIG.18A
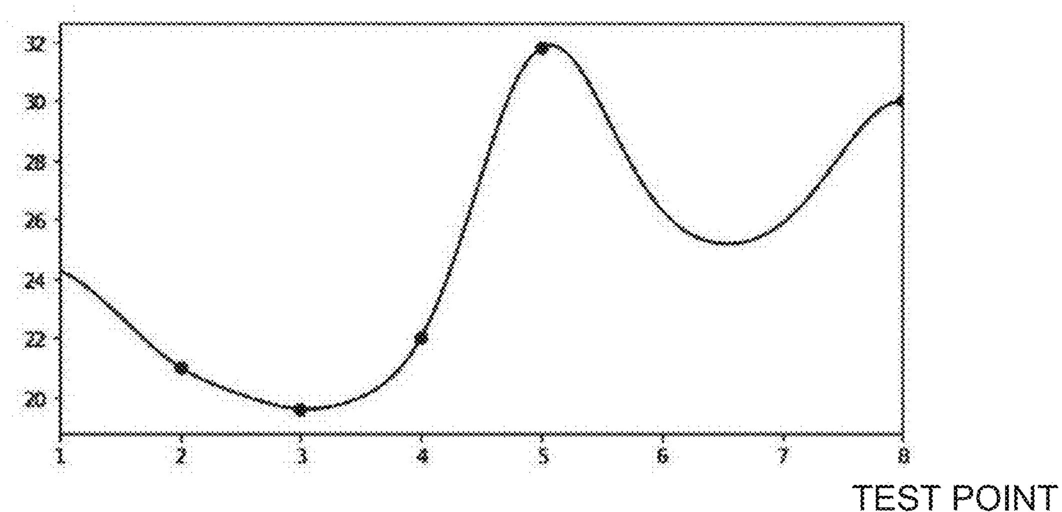

FIG.18B
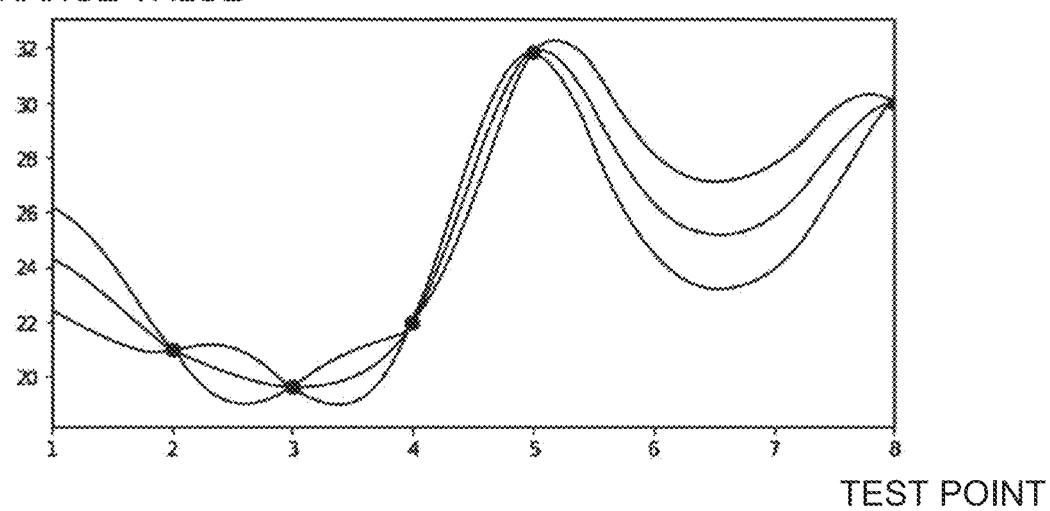

ESTIMATED
LUMINANCE VALUE

TEST POINT

VISUAL FIELD TESTING METHOD, VISUAL FIELD TESTING DEVICE, AND VISUAL FIELD TESTING PROGRAM

CROSS-REFERENCE TO RELATED APPLICATION

This application is a continuation application of International Application No. PCT/JP2022/023856, filed Jun. 14, 2022, the disclosure of which is incorporated herein by reference in its entirety. Further, this application claims priority from Japanese Patent Application No. 2021-100268, filed Jun. 16, 2021, the disclosure of which is incorporated herein by reference in its entirety.

TECHNICAL FIELD

The technology of the present disclosure relates to a visual field testing method, a visual field testing device, and a visual field testing program.

BACKGROUND ART

Japanese Patent No. 5048284 discloses a visual field testing device that tests sensitivity to light stimulation to an eye to be tested. A need exists for a visual field testing device that does not impose a burden on a subject.

SUMMARY OF INVENTION

A visual field testing method of a first aspect of the technology of the disclosure is a visual field testing method of testing a visual field range divided into at least a first partial area and a second partial area, the method including: a step of measuring sensitivities of a plurality of first test points that are included in the first partial area; and a step of performing a process of estimating sensitivities of a plurality of second test points that are included in the first partial area and are test points other than the first test points, by using the sensitivities of the plurality of first test points.

A visual field testing device of a second aspect of the technology of the disclosure is a visual field testing device including a processor, and configured to test a visual field range divided into at least a first partial area and a second partial area, the processor performing: a step of measuring sensitivities of a plurality of first test points that are included in the first partial area; and a step of performing a process of estimating sensitivities of a plurality of second test points that are included in the first partial area and are test points other than the first test points, by using the sensitivities of the plurality of first test points.

A program of a third aspect of the technology of the disclosure causes a computer to execute: a step of measuring, in a visual field range divided into at least a first partial area and a second partial area, sensitivities of a plurality of first test points that are included in the first partial area; and a step of performing a process of estimating sensitivities of a plurality of second test points that are included in the first partial area and are test points other than the first test points, by using the sensitivities of the plurality of first test points.

BRIEF DESCRIPTION OF DRAWINGS

FIG. 2 is a block diagram illustrating a configuration of a perimeter 110.

FIG. 9 is a flowchart of a visual field testing process executed by the CPU 22 of the perimeter 110.

FIG. 14C is a schematic view illustrating setting of additional test points in the case of no abnormality.

FIG. 18A is a graph illustrating an estimated luminance value of each test point of an entire test point set.

FIG. 18B is a graph in which reliability is added to the graph of FIG. 18A.

DESCRIPTION OF EMBODIMENTS

Hereinafter, an embodiment of the technology of the present disclosure will be described in detail with reference to the diagram.

Figure 1:
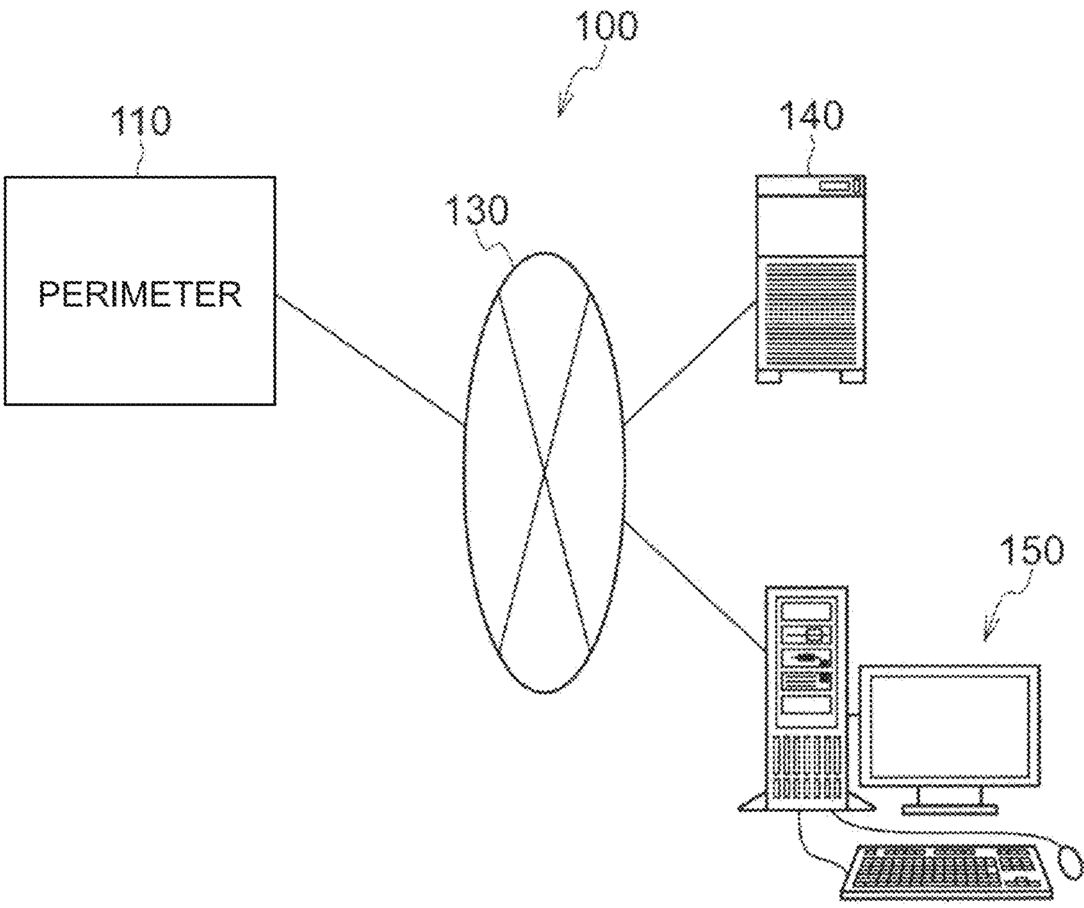
FIG. 1 is a block diagram of an ophthalmic system 100.

A configuration of an ophthalmic system 100 will be described with reference to FIG. 1. As illustrated in FIG. 1, the ophthalmic system 100 includes a static visual field testing device (hereinafter referred to as "perimeter") 110, a management server device (hereinafter referred to as "server") 140, and an image display device (hereinafter referred to as "viewer") 150.

The perimeter 110 is an example of a "visual field testing device" of the technology of the disclosure.

The perimeter 110 is a device that tests a visual field sensitivity (luminance value) of an eye to be tested of a subject, which will be described in detail later, and is used for diagnosis of glaucoma, retinitis pigmentosa, and the like.

The visual field sensitivity is an intensity of indicator light (luminance value: luminance (dB)) that has reached a test point to be tested in the optic nerve present in the retina of an eye to be tested and has been recognized by a subject. The larger the luminance value expressed in dB, the smaller the intensity of indicator light reaching a test point. In other words, the smaller the luminance value expressed in dB, the larger the intensity of indicator light reaching a test point. That is, the larger the luminance value expressed in dB, the darker the indicator light, and the smaller the luminance value expressed in dB, the brighter the indicator light.

The server 140 stores a test result (estimated sensitivity or the like) of the visual field sensitivity of an eye to be tested of a subject by the perimeter 110 in association with a patient ID. The viewer 150 displays medical information such as the test result of the visual field sensitivity of an eye to be tested acquired from the server 140.

The perimeter 110, the server 140, and the viewer 150 are mutually connected via a network 130.

FIG. 2 illustrates a configuration of the perimeter 110.

A horizontal direction in a case in which the perimeter 110 is installed on a horizontal plane is defined as an "X direction", a vertical direction with respect to the horizontal plane is defined as a "Y direction", and a direction connecting the center of the pupil in the anterior eye segment of an eye to be tested 12 and the center of the eyeball is defined as a "Z direction". Therefore, the X direction, the Y direction, and the Z direction are perpendicular to each other. As illustrated in FIG. 2, the perimeter 110 includes a control device 10, an indicator presentation unit 30, an external storage device 40, an input/display unit 50, and a response unit 60.

The control device 10 includes a computer including a central processing unit (CPU) 22, a read-only memory (ROM) 24, a random access memory (RAM) 26, and an input/output (I/O) port 28, which are mutually connected by a bus 20. The ROM 24 stores a visual field testing program described later.

The CPU 22 is an example of a "processor" of the technology of the disclosure. The processor executes the visual field testing program.

The indicator presentation unit 30, the external storage device 40, a communication interface (I/F) 45, the input/display unit 50, and the response unit 60 are connected to the I/O port 28.

The input/display unit 50 has a graphic operator interface for displaying an image and receiving various instructions from an operator. Examples of the graphic operator interface include a touch panel display.

The response unit 60 includes a switch (not illustrated) to be operated by a subject (patient), and a transmitter. In a case in which a subject recognizes indicator light in a visual field test described later, the subject turns on the switch. In a case in which the switch is turned on, the transmitter transmits a recognition signal indicating that a subject has recognized indicator light to the control device 10.

The communication interface (I/F) 45 is connected to the server 140 and the viewer 150 via the network 130.

The indicator presentation unit 30 includes a dome 30D the hemispherical inner surface of which is a reflecting surface, and a projector (not illustrated) that presents an indicator (specifically, projects light) at points at a plurality of positions on the inner surface of the dome 30D. Under the control of the control device 10 according to the visual field testing program for a visual field test described later, the projector presents an indicator at points (indicator presentation points) at a plurality of different positions on the inner surface of the dome 30D at shifted timings. The indicator presentation points correspond to the retina of an eye to be tested. Indicator light from the indicator presentation point reaches a test point in the retina of the eye to be tested 12. As described above, a subject who has recognized indicator light turns on the switch, and the transmitter transmits a recognition signal to the control device 10.

In the technology of the disclosure, a configuration of the indicator presentation unit 30 is not limited to a configuration including the dome 30D and the projector. In the technology of the disclosure, it is possible to adopt, for example, a configuration in which a point on the inner surface of the dome 30D emits light by itself, or a configuration in which indicator light is directly presented to a test point in the retina of the eye to be tested 12, as the configuration of the indicator presentation unit 30.

The server 140 and the viewer 150 include: a computer including a CPU, a RAM, a ROM, and other components; an input device; a display; and an external storage device or the like.

Figure 3:
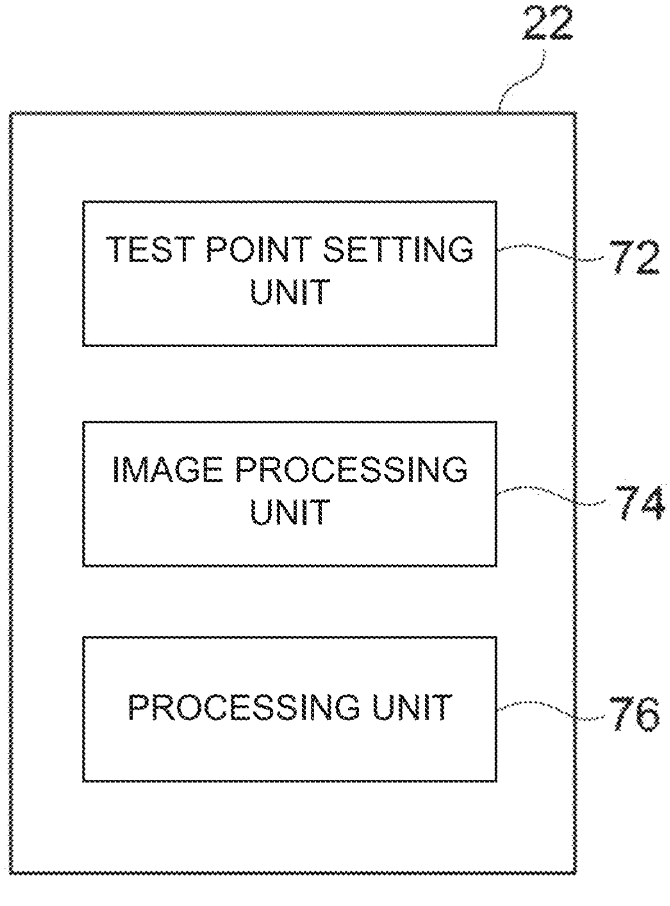
FIG. 3 is a functional block diagram of a CPU 22 of the perimeter 110.

FIG. 3 illustrates a functional block diagram of the CPU 22 of the perimeter 110. Various functions realized by the CPU 22 of the perimeter 110 executing the visual field testing program will be described. The visual field testing program has a test point setting function, an image processing function, and a processing function. As a result of the CPU 22 executing the visual field testing program having each of these functions, the CPU 22 functions as a test point setting unit 72, an image processing unit 74, and a processing unit 76 as illustrated in FIG. 3.

Figure 4A:
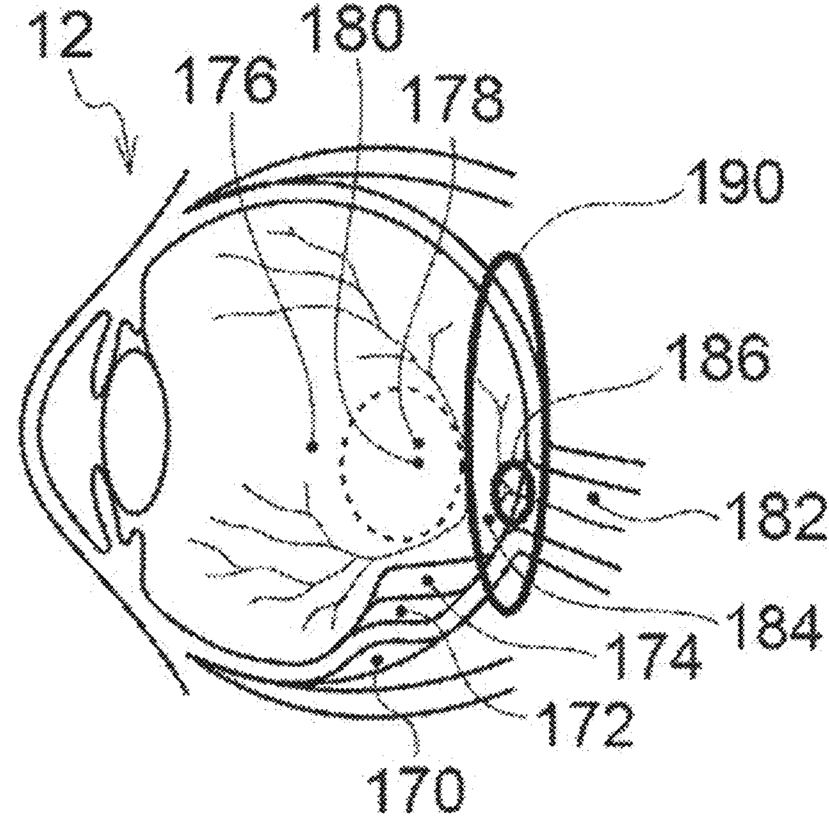
FIG. 4A is an explanatory view illustrating a structure of an eye to be tested 12.

FIG. 4A is an explanatory view illustrating a structure of the eye to be tested 12. The eyeball forming the eye to be tested 12 has a substantially spherical shape surrounded by a sclera 170. A choroid 172 is inside the sclera 170, and a retina 174 is further inside the choroid 172. The inside of the eyeball covered by the retina 174 is filled with a gel-like vitreous body 176.

The retina 174 has visual cells arranged in a planar manner. The visual cells convert a visual image (optical information) into a nerve signal (electrical signal). The nerve signal obtained by the visual cells is transmitted from an optic nerve head 184 to a brain through an optic nerve 182.

An area in the retina 174 where the visual cells are densely arranged is a macula 178. A fovea 180 corresponding to the center of the macula 178 has the highest resolution in a visual field because the visual cells are most densely arranged. Since the optic nerve head 184 is a portion where the optic nerve 182 converges, there is no visual cell in the optic nerve head 184. As a result, an area on the retina 174 where the optic nerve head 184 exists becomes a blind spot 186.

In the present embodiment, the visual field sensitivity of the eye to be tested 12 is measured, and an area where the visual cells are significantly arranged on the retina 174 of the fundus is set as a test target area 190.

Figure 4B:
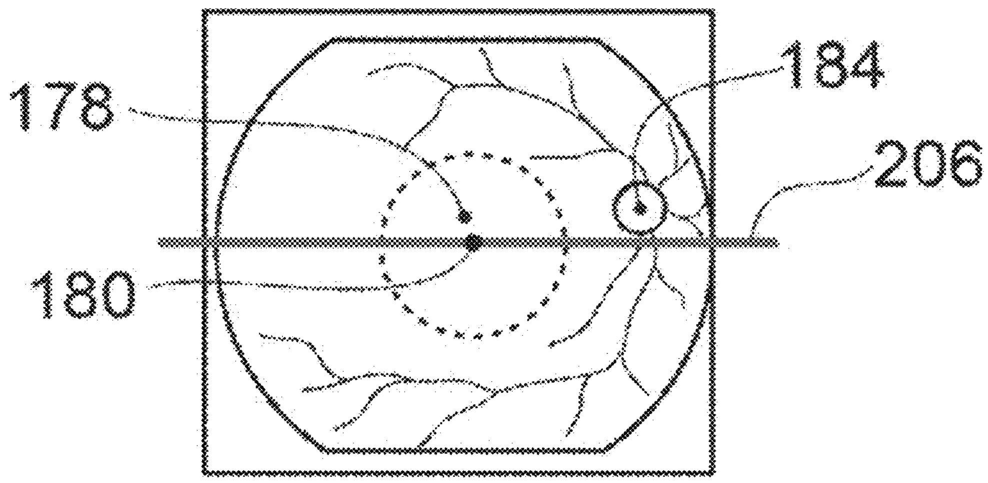
FIG. 4B is an image of a test target area 190 in a normal fundus.

FIG. 4B is an image of the test target area 190 in the normal fundus of a right eye. A horizontal line crossing the image is a horizontal meridian 206, which is a boundary line between an upper area 202 and a lower area 204 in a visual field test area. In the present embodiment, test data is interpolated independently in each of the upper area 202 and the lower area 204 of the fundus as described later.

Figure 4C:
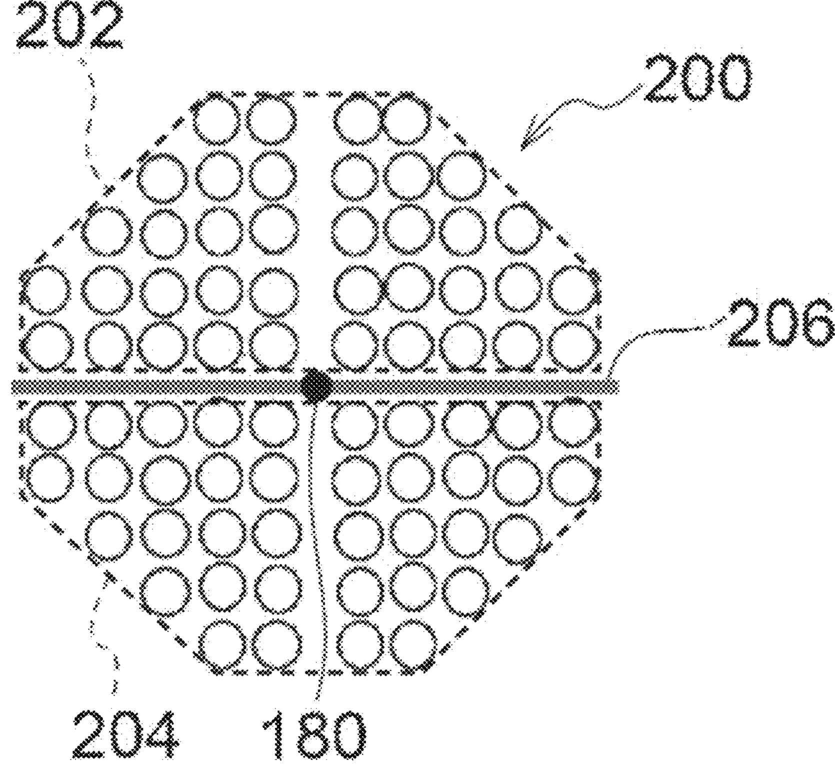
FIG. 4C is a schematic view illustrating a test point set 200 that is a set of test points to which indicator light is presented in the test target area 190.

FIG. 4C is a schematic view illustrating a test point set 200 that is a set of test points to which indicator light is presented in the test target area 190. There are a large number of test points included in the test point set 200. Therefore, in the present embodiment, a thinned-out test is performed in which a subject's reaction is acquired by presenting indicator light to some selected test points, and a luminance value of a test point to which no indicator light is presented is interpolated by a method such as Gaussian process regression. As will be described later, there is a fundus disease case in which continuity between the upper area 202 and the lower area 204 is weak. Data interpolation such as Gaussian process regression is easily affected by data of a test point adjacent to a test point as an interpolation target. When there is actually no disease in the upper area 202, but a disease is observed at a test point in the lower area 204 adjacent to the upper area 202, if data interpolation is performed in the upper area 202 and the lower area 204 together, there is a risk that data interpolation is performed such that a normal test point also has a disease. In the present embodiment, erroneous interpolation as described above is inhibited by performing data interpolation independently in the upper area 202 and the lower area 204, for example.

The case means a visual field defect case in glaucoma. Specifically, there are cases such as a nasal breakthrough, a nasal step, a temporal wedge defect, and an arcuate scotoma.

Figure 4D:
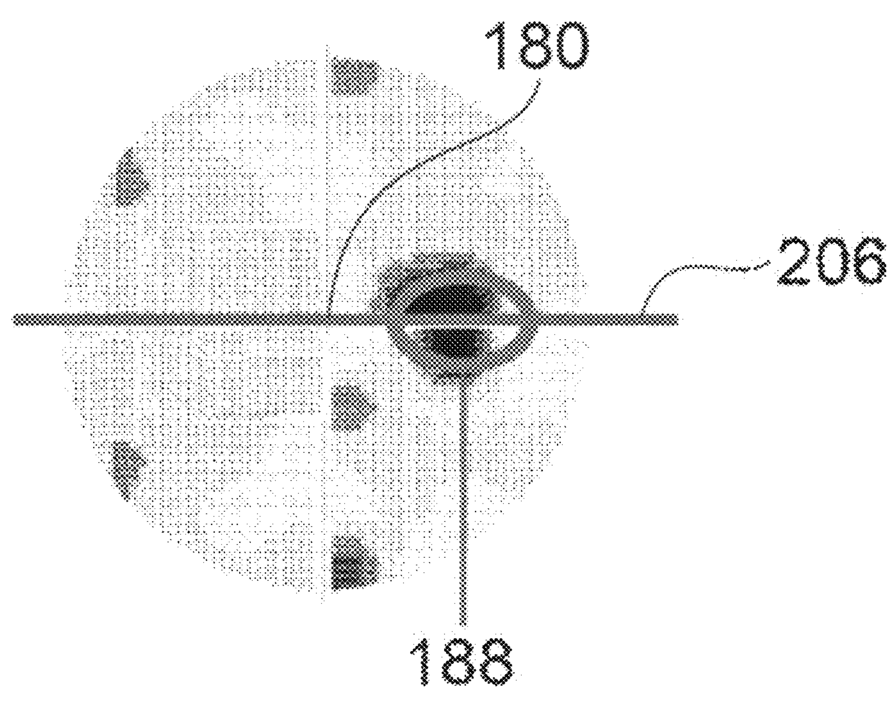
FIG. 4D is a visual field sensitivity map illustrating a result of a visual field test of a normal fundus.

FIG. 4D is a visual field sensitivity map illustrating a result of a visual field test of the normal fundus of a right eye. In the visual field sensitivity map, an area having a low luminance value indicating the visual field sensitivity is indicated as a dark spot. Although there is a dark spot 188 in FIG. 4D, the dark spot 188 corresponds to the optic nerve head 184 that is the blind spot 186.

Figure 5A:
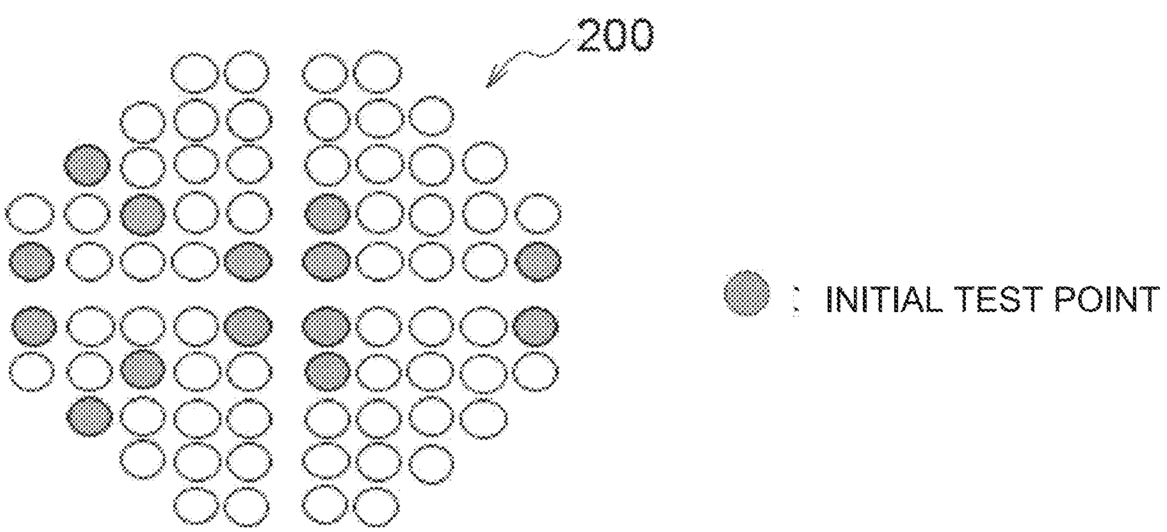
FIG. 5A is an explanatory view illustrating that initial test points are set from the test point set 200.

FIGS. 5A to 5E are explanatory views schematically illustrating a visual field test. In the present embodiment, an initial test point indicated in gray is set from the test point set 200 as illustrated in FIG. 5A after the visual field test is started. The test point set 200 is a plurality of test points disposed respectively over a range of, for example, the optic nerve of the retina of the eye to be tested 12 that is reached by indicator light through the pupil of the eye to be tested 12, and is a set of test points to be tested for the visual field sensitivity. In the present embodiment, a thinned-out test is performed in which visual field sensitivities of not all the test points included in the test point set 200 but of test points with high priority are measured by setting some initial test points from the test point set 200.

Basically, the initial test points do not depend on the presence or absence of past diagnostic data of a subject, and the same initial test points are set in both the cases of the presence and absence of the past diagnostic data. However, the initial test points may be set according to past diagnostic data of a subject. For example, in a case in which it is described that there is an area having a low visual field sensitivity in the past diagnostic data, the initial test points may be intensively set in an area including this area. The initial test points need not be set vertically symmetrically as illustrated in FIG. 5A, and may be set asymmetrically.

Figure 5B:
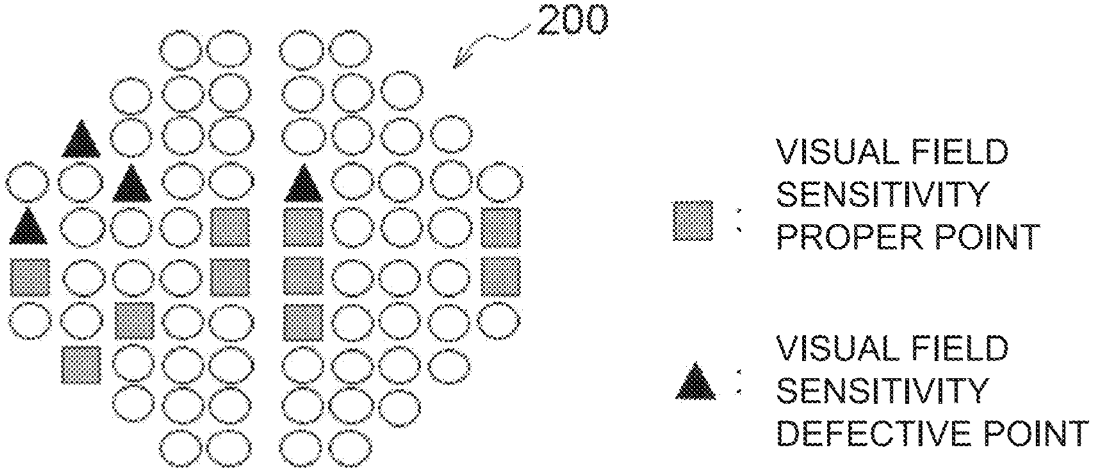
FIG. 5B is an explanatory view illustrating a result of testing the initial test points.

FIG. 5B is an explanatory view illustrating a result of testing the initial test points. In FIG. 5B, a test point indicated by a black triangle is a visual field sensitivity defective point at which the visual field sensitivity has a predetermined threshold or smaller, and another test point indicated by a square is a visual field sensitivity proper point at which the visual field sensitivity exceeds the predetermined threshold.

Figure 5C:
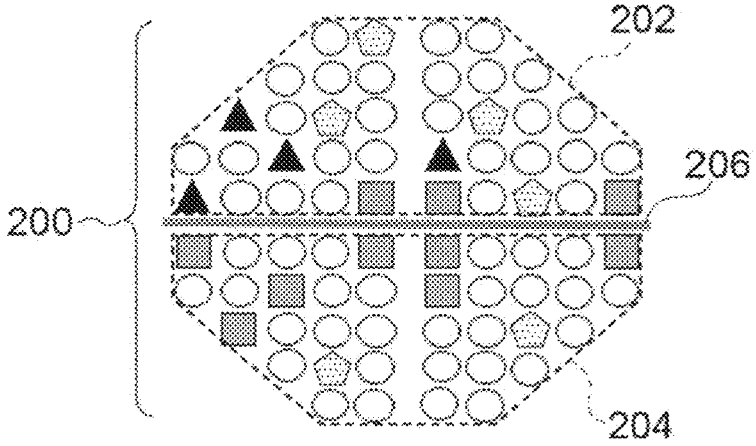
FIG. 5C is an explanatory view illustrating an example of a case in which additional test points are set on the basis of the test result.

FIG. 5C is an explanatory view illustrating an example of a case in which additional test points are set on the basis of the test result. In FIG. 5C, the fundus of the eye to be tested 12 is divided into the upper area 202 and the lower area 204 by the horizontal meridian 206 passing through the fovea corresponding to the center of the macula in the fundus. Since many visual field sensitivity defective points exist in the upper area as illustrated in FIG. 5C, additional test points indicated by pentagons are preferentially set in the upper area 202 rather than in the lower area 204.

Figure 5D:
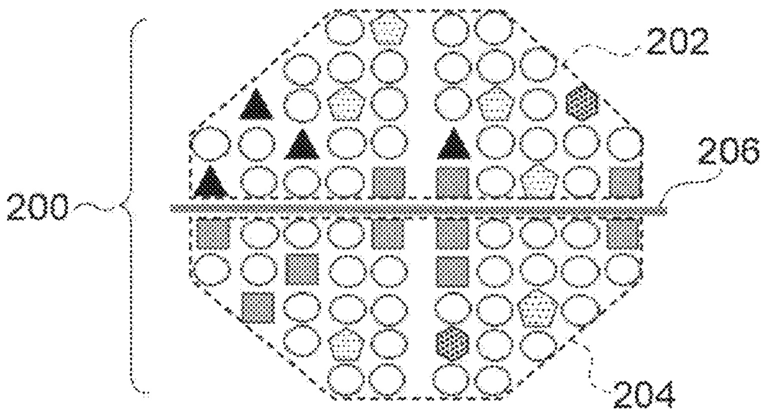
FIG. 5D is an explanatory view illustrating a case in which additional test points are further set.

FIG. 5D is an explanatory view illustrating a case in which additional test points are further set. In a case in which additional test points are further set, and the additional test points having been previously set are preferentially set in an area where many visual field sensitivity defective points exist, the same number of additional test points indicated by hexagons are set in the upper area 202 and the lower area 204 as illustrated in FIG. 5D. Alternatively, the new additional test points may be preferentially set in an area where many visual field sensitivity defective points exist.

Figure 5E:
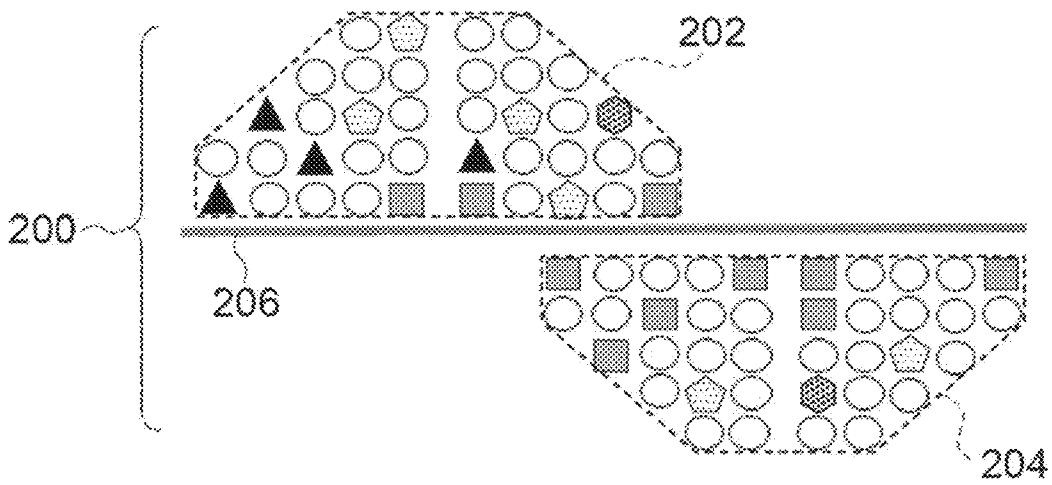
FIG. 5E is an explanatory view of a case in which visual field sensitivities of untested points indicated by white circles in a visual field test area are estimated on the basis of the test result.

FIG. 5E is an explanatory view of a case in which visual field sensitivities of untested points indicated by white circles in a visual field test area are estimated on the basis of the test result. In the present embodiment, the visual field test area is divided into the upper area 202 and the lower area 204, and test data is interpolated independently in each of the areas as illustrated in FIG. 5E.

Figure 6:
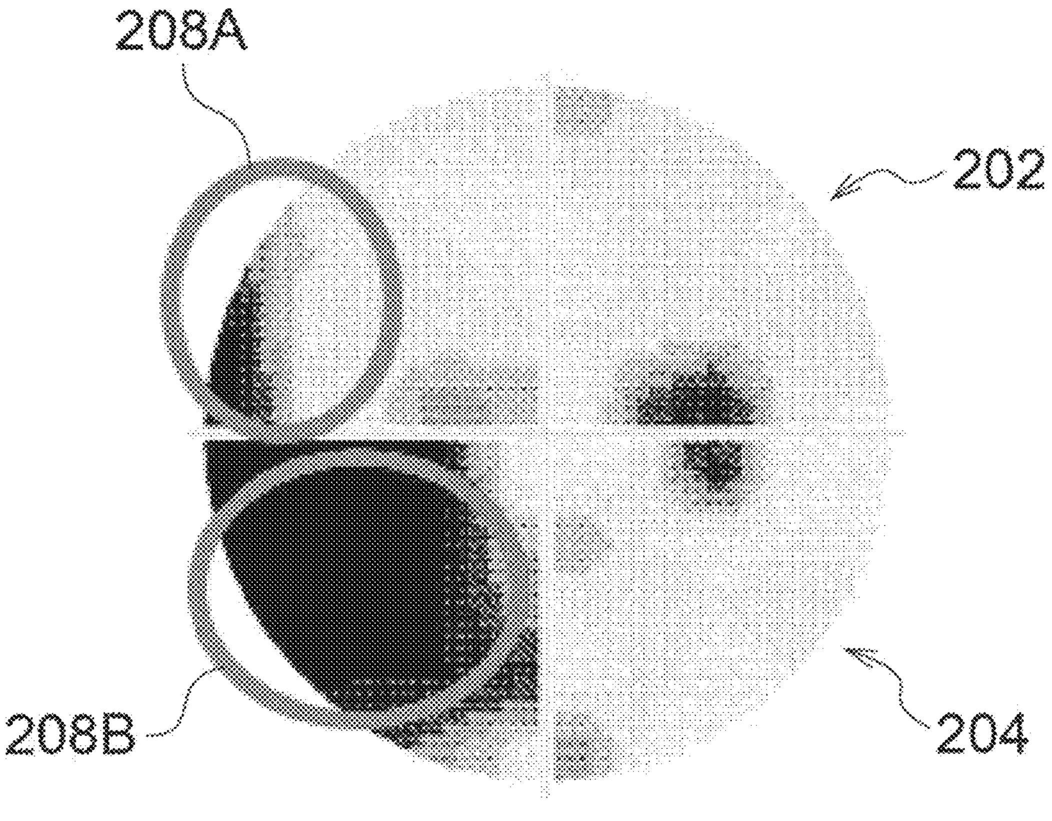
FIG. 6 is a schematic view illustrating an example of a visual field sensitivity map of a fundus having a disease.

FIG. 6 is a schematic view illustrating an example of a visual field sensitivity map of a fundus having a disease. An area 208A indicating an upper visual field defect exists in the upper area 202 of the visual field sensitivity map, and an area 208B indicating a lower visual field defect exists in the lower area 204. In FIG. 6, no noticeable continuity is observed between the area 208A indicating an upper visual field defect and the area 208B indicating a lower visual field defect. In a case in which data interpolation is performed in the entire test point set 200 in such a situation, there is a risk that the area 208A indicating an upper visual field defect becomes larger than a state illustrated in FIG. 6.

Figure 7:
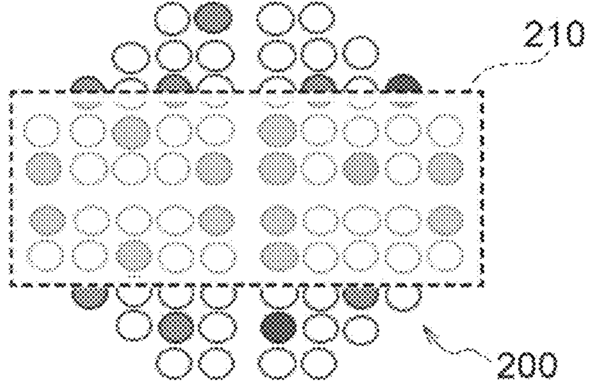
FIG. 7 is an explanatory view illustrating correlation of data interpolation in an upper area 202 and a lower area 204 in a case in which it is assumed that test data is interpolated in an entire visual field test area of a fundus.

FIG. 7 is an explanatory view illustrating correlation of data interpolation in the upper area 202 and the lower area 204 in a case in which it is assumed that test data is interpolated in an entire visual field test area of a fundus. Some visual field defect cases have a significant difference in the upper area 202 or the lower area 204. In a case in which data interpolation of test points existing in the upper area 202 and the lower area 204 is performed in such a case, a result of the interpolation has correlation between the upper area 202 and the lower area 204. There is a risk that a test point that is originally a visual field sensitivity proper point is interpolated as a visual field sensitivity defective point particularly in a correlation area 210 extending over the upper area 202 and the lower area 204 as illustrated in FIG. 7.

In the present embodiment, test data is independently interpolated in the upper area 202 and the lower area 204, as a result of which inappropriate interpolation due to the correlation between the respective areas is inhibited.

Figure 8A:
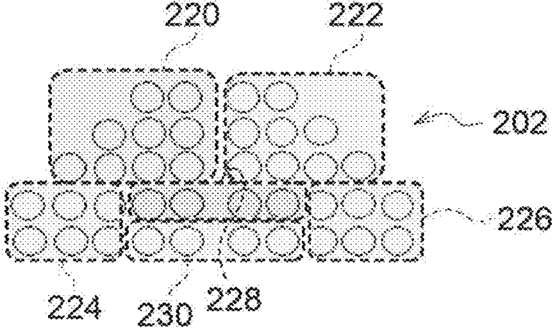
FIG. 8A is an explanatory view illustrating a case in which the upper area 202 is subdivided into areas 220, 222, 224, 226, 228, and 230, and test data is interpolated independently in each of the areas.

The visual field test area may be not only divided into the upper and lower areas by the horizontal meridian 206 passing through the fovea as illustrated in FIG. 5A, but, for example, the upper area 202 may also be subdivided into areas 220, 222, 224, 226, 228, and 230, and test data may be interpolated independently in each of the areas, as illustrated in FIG. 8A.

Figure 8B:
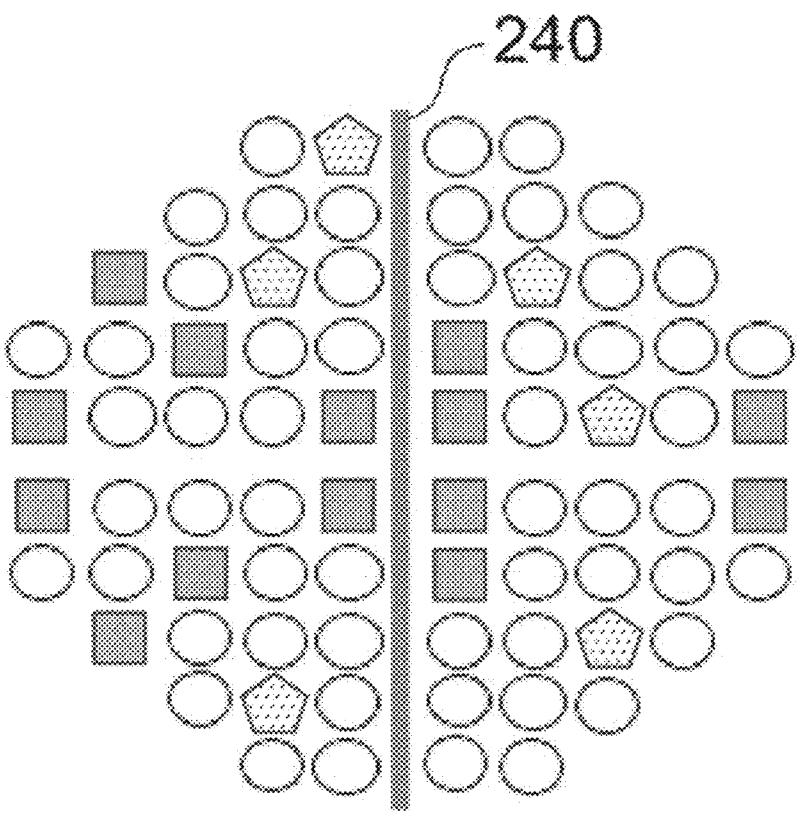
FIG. 8B is a schematic view of a case in which a visual field test area is divided into two right and left areas by a vertical meridian 240 passing through a fovea.
Figure 8C:
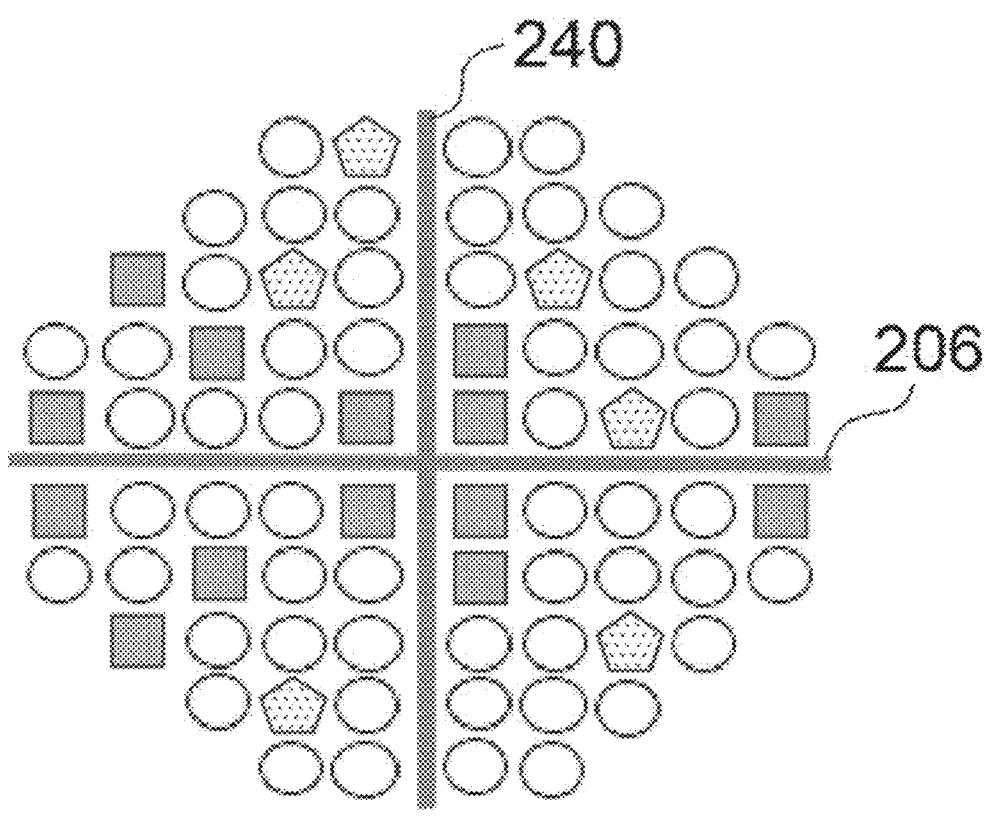
FIG. 8C is a schematic view of a case in which a visual field test area is divided into four upper, lower, right, and left areas by a horizontal meridian 206 passing through a fovea and the vertical meridian 240 passing through the fovea.

The visual field test area may also be divided into two right and left areas by a vertical meridian 240 passing through the fovea as illustrated in FIG. 8B. Alternatively, the visual field test area may be divided into four upper, lower, right, and left areas by the horizontal meridian 206 passing through the fovea and the vertical meridian 240 passing through the fovea as illustrated in FIG. 8C.

FIG. 9 illustrates a flowchart of a visual field testing process executed by the CPU 22 of the perimeter 110. As a result of the CPU 22 executing the visual field testing program, the visual field testing process illustrated in the flowchart of FIG. 9 is realized. The visual field testing process is started after a start button (not illustrated) displayed on the input/display unit 50 is operated by an operator.

In step 100, the image processing unit 74 displays an input screen for a patient ID on the input/display unit 50. The operator inputs a patient ID to the input/display unit 50. In step 102, the processing unit 76 acquires the patient ID.

In step 104, the test point setting unit 72 inquires of the server 140 whether test results of visual field sensitivities corresponding to the acquired patient ID are stored. That is, the test point setting unit 72 inquires whether test results of visual field sensitivities are stored corresponding to the acquired patient ID. The test point setting unit 72 acquires an inquiry result from the server 140, and determines whether or not there is past data of the test results of visual field sensitivities corresponding to the patient ID on the basis of the acquired inquiry result. The past data is data for each subject according to test points of each subject. The past data is, for example, the visual field sensitivities of the patient, or an estimated sensitivity of each test point, the number of tests, and a cumulative function described later. The past data may be acquired data of all tests performed in the past, or may be data updated after the latest test.

In a case in which it is determined in step 104 that the past data of the test results of visual field sensitivities corresponding to the patient ID exists, the processing unit 76 reads the latest estimated sensitivity (visual field sensitivity) of each test point of the test point set 200 and the number of tests from the past data corresponding to the input patient ID in step 106. In a case in which it is determined in step 104 that there is no past data of the test results of visual field sensitivities corresponding to the patient ID, the processing unit 76 reads a prescribed luminance value for each test point of the test point set 200 in step 108. The prescribed luminance value is, for example, a reference value for each test point of the test point set 200 in a normal eye.

In step 110, the test point setting unit 72 sets a set of initial test points as illustrated in FIG. 5A. In step 112, the test point setting unit 72 selects luminance values of indicator light to be presented to the initial test points set in step 110. In step 112, the luminance values may be, for example, selected randomly, may be selected by an operator, or may be automatically selected on the basis of past data.

Figure 11A:
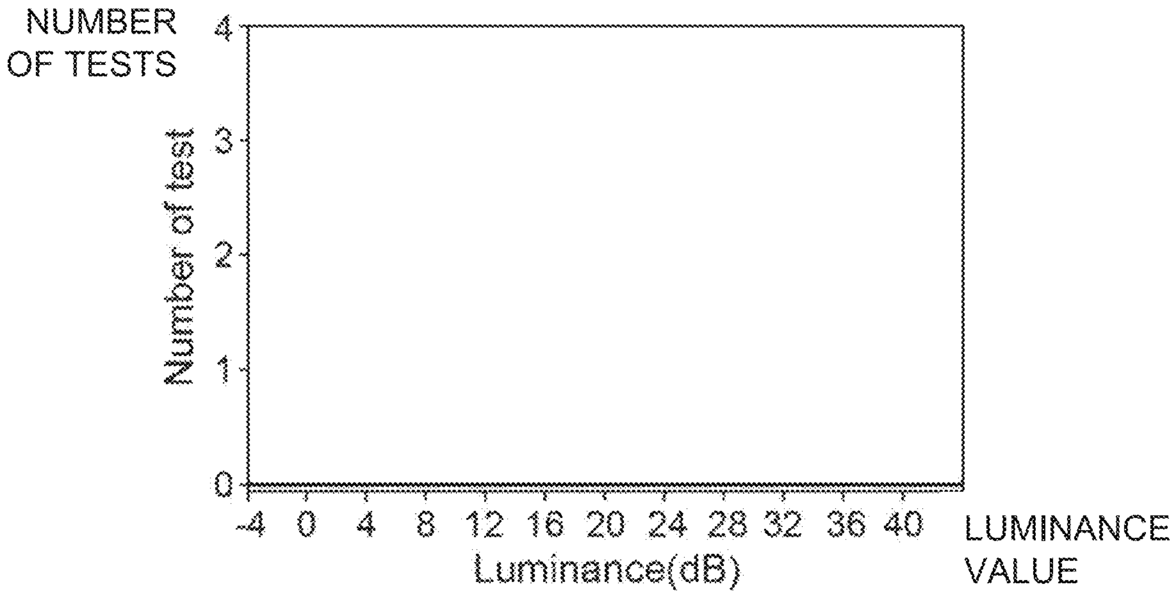
FIG. 11A is a diagram illustrating an updating process of a cumulative function.

In step 114, a cumulative function is initialized. The cumulative function is a function indicating a relationship between a luminance value of indicator light and the number of tests, and more specifically, is a function that associates the cumulative number of times used in a test with each luminance value of indicator light. The initialization of the cumulative function is a process of setting the number of tests corresponding to each luminance value to 0 as illustrated in FIG. 11A. The cumulative function will be described later with reference to FIGS. 11A to 11I.

In step 116, one test point is selected from the set of initial test points set in step 110. The test point may be selected randomly from the set of initial test points, may be selected by an operator, or may be automatically selected on the basis of past data.

In step 118, the cumulative number of tests of the test point selected in step 116 is acquired. The cumulative number of tests can be extracted from the cumulative function described later, but may be held as data independent of the cumulative function as the cumulative number of tests.

In step 120, it is determined whether or not the cumulative number of tests is 1 or more. In a case in which the cumulative number of tests is 1 or more in step 120, the procedure proceeds to step 122. In a case in which the cumulative number of tests is less than 1, the procedure proceeds to step 124.

In step 122, indicator light having a luminance value based on the cumulative function s presented to the test point selected in step 116. The test point setting unit 72 sets the luminance value of the presented indicator light from a range of luminance values extracted from the cumulative function. In the technology of the disclosure, the luminance value of the presented indicator light may be randomly extracted and set, or an optionally determined value may be extracted and set, from the range of the extracted luminance values. For example, the test point setting unit 72 may extract, from this range, a median value, a value of ¾, or the like in the range as the luminance value of the presented indicator light. Next, the test point setting unit 72 controls the projector such that the indicator light of the extracted luminance value is incident on the test point selected in step 116.

In step 124, indicator light of the initial luminance value set in step 112 is presented to the subject.

In step 126, the test point setting unit 72 acquires a reaction of the subject. In a case in which the subject recognizes the indicator light presented in step 122 or step 124, the subject turns on the switch of the response unit 60. As a result, a recognition signal is transmitted to the control device 10. In a case in which the subject does not recognize the indicator light when presented with the indicator light, the subject does not turn on the switch of the response unit 60. The test point setting unit 72 determines whether or not the subject recognizes the indicator light on the basis of whether or not the recognition signal is transmitted before the elapse of a predetermined time from the presentation of the indicator light. For example, in a case in which the recognition signal is transmitted before the elapse of a predetermined time from the presentation of the indicator light, the test point setting unit 72 acquires a reaction of the subject that the subject recognizes the indicator light. In a case in which the recognition signal is not transmitted even after the lapse of the predetermined time, the test point setting unit 72 acquires a reaction of the subject that the subject does not recognize the indicator. The test point setting unit 72 stores the reaction of the subject acquired in step 126 in the external storage device 40.

In step 128, the test point setting unit 72 updates the cumulative function. In the present embodiment, the processes from step 116 to step 128 are repeated, and the cumulative function updating process in step 128 is also repeated. The cumulative number of test is also updated. By repeating the processes from step 116 to step 128, indicator light having different luminance values is presented a plurality of times to each test point belonging to the set of initial test points set in step 110, and the reaction of the subject to each indicator light is obtained. Therefore, the cumulative function corresponding to each test point is updated on the basis of the reaction of the subject in each presentation. Hereinafter, a specific description will be given.

Figure 11B:
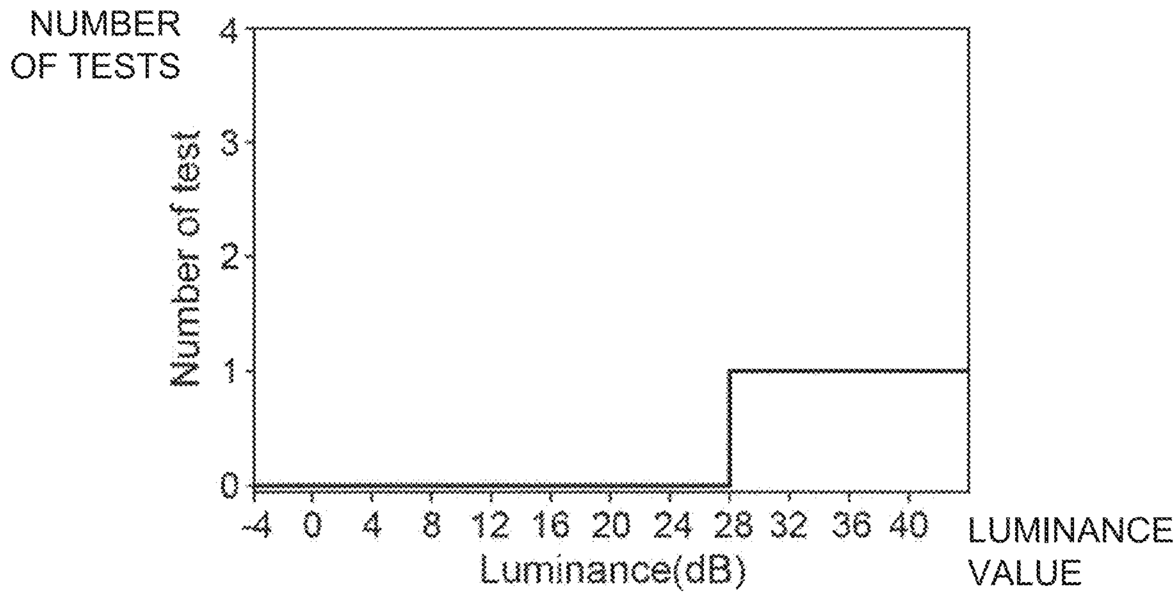
FIG. 11B is another diagram illustrating an updating process of a cumulative function.

For the cumulative function, in a case in which there is no past data, the cumulative number of tests before a test is 0 for each luminance value as illustrated in FIG. 11A, and there is no cumulative function. For example, indicator light having an initial luminance value of 28 dB is presented to the subject by the process in step 124. In a case in which the subject does not recognize this indicator light, the test point setting unit 72 increases the number of tests for each luminance value in a range determined with 28 dB as a boundary, that is, a range of 28 dB or more, by a predetermined amount as illustrated in FIG. 11B. The predetermined amount to be increased is, for example, 1. Therefore, the number of tests for each luminance value in the range of 28 dB or more is 1 as illustrated in FIG. 11B.

The reason why the number of tests for each luminance value in the range of 28 dB or more is set to 1 even though only the luminance value of 28 dB is presented in FIG. 11B is as follows. In a case in which the subject does not recognize the indicator light of 28 dB, it is estimated that the subject cannot recognize indicator light having a luminance value larger than 28 dB, that is, light darker than the presented indicator light. Therefore, it is estimated that a subject's reaction is obtained that an indicator light having a luminance value larger than 28 dB cannot be recognized at the test point presented with the indicator light of 28 dB. Thus, the subject's reaction is assumed without actually performing a test for the luminance value larger than 28 dB, whereby the number of tests is increased by 1 on the assumption that the test has been performed. The predetermined amount to be increased may be a value different according to each luminance value. For example, in a case in which the subject does not recognize the indicator light of 28 dB, the number of tests may be increased by 1 for each luminance value in a range of from 28 dB to less than 32 dB, the number of tests may be increased by 2 for each luminance value in a range of from 32 dB to less than 36 dB, and the number of tests may be increased by 3 for each luminance value in a range of 36 dB or more. This corresponds to performing an operation of increasing the number of tests for each luminance value described above by 1 with respect to three tests including a pseudo test assuming that the subject cannot recognize all indicator light in a case in which indicator light of 32 dB and indicator light of 36 dB are presented in a pseudo manner in addition to the indicator light of 28 dB.

In a case in which the number of tests is 1 in step 128, the cumulative function is updated as illustrated in FIG. 11B.

In step 130, it is determined whether or not the visual field sensitivity can be estimated with sufficient accuracy for the set of test points selected in step 116. In the present embodiment, it is determined whether or not the cumulative function forms a downwardly projecting linear shape as in FIG. 11I, and the luminance of indicator light that can be recognized by the subject can be estimated with sufficient accuracy as described later. In a case in which the number of tests is 1, the cumulative function does not form a downwardly projecting linear shape as illustrated in FIG. 11B, and thus, the visual field sensitivity cannot be estimated with sufficient accuracy.

In order to estimate the visual field sensitivity in step 130, subject's reactions are acquired by presenting indicator light having different luminance values to the test point selected in step 116, and the cumulative function is updated according to the luminance values of the presented indicator light and the subject's reactions.

Figure 11C:
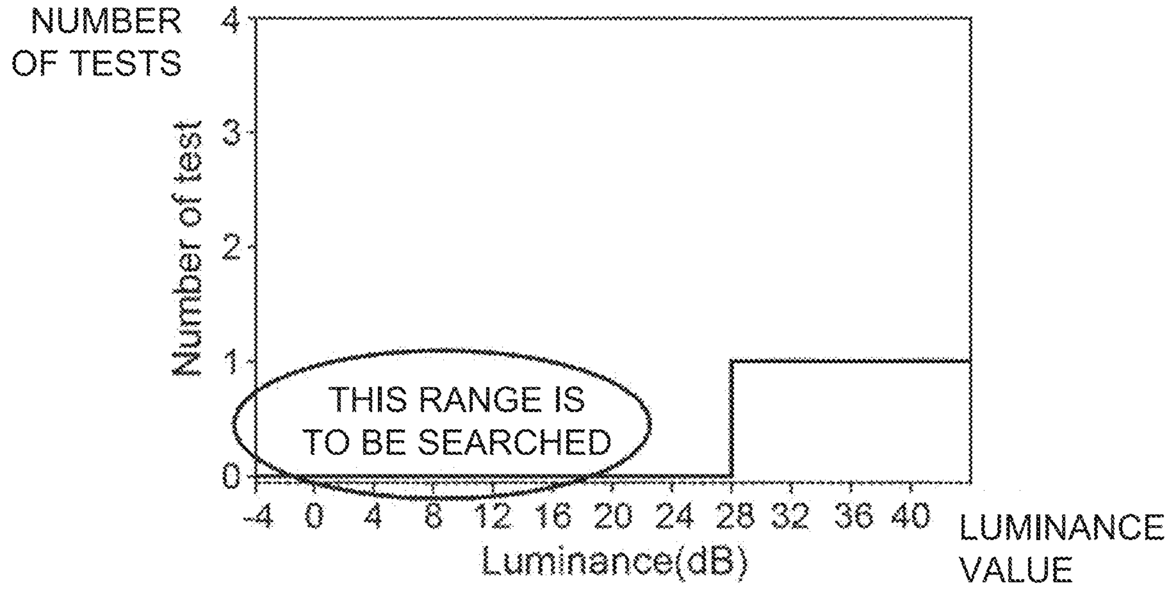
FIG. 11C is another diagram illustrating an updating process of a cumulative function.

For example, in a case in which the result illustrated in FIG. 11B is obtained, it is unknown whether or not a range of luminance values smaller than 28 dB can be recognized for the test point selected in step 116 as illustrated in FIG. 11C. Thus, it is necessary to search (test) whether or not the range of luminance values smaller than 28 dB can be recognized.

Figure 11D:
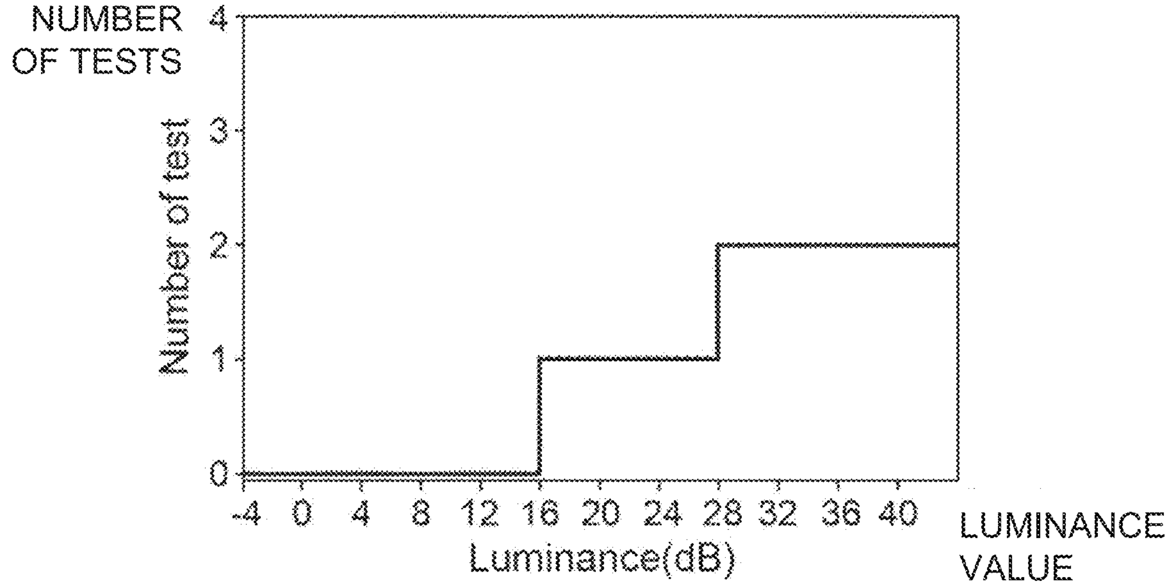
FIG. 11D is another diagram illustrating an updating process of a cumulative function.
Figure 11E:
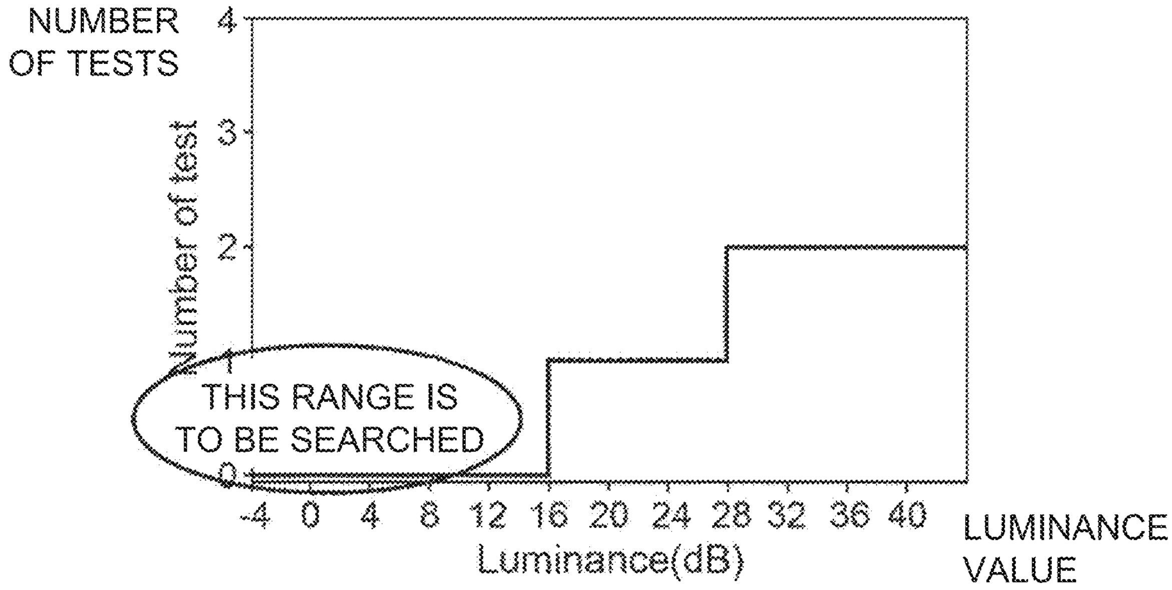
FIG. 11E is another diagram illustrating an updating process of a cumulative function.
Figure 11F:
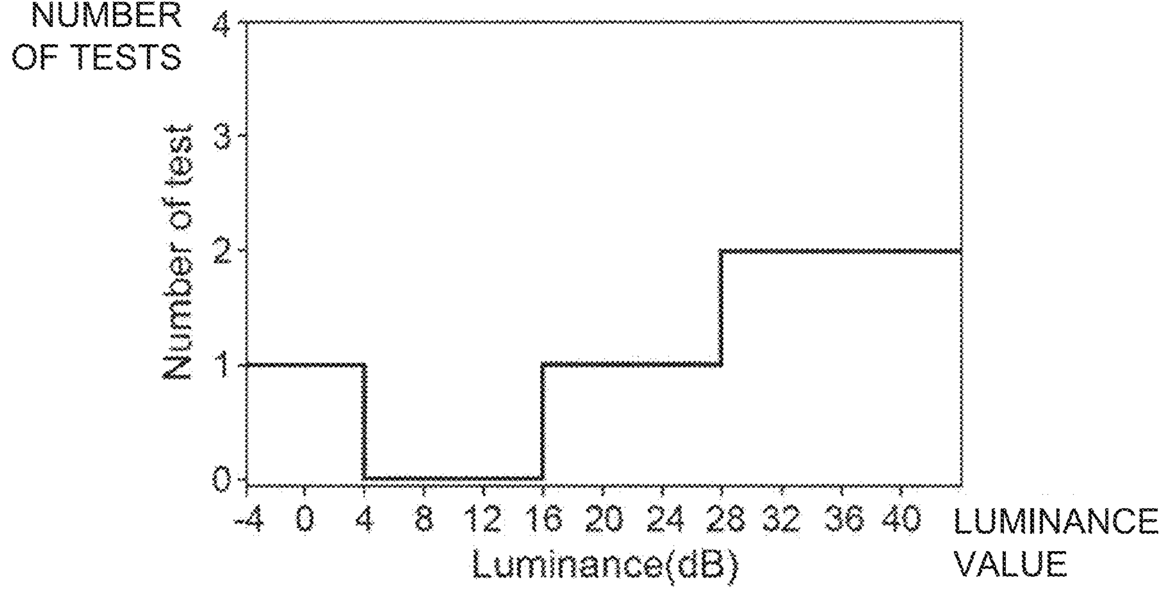
FIG. 11F is another diagram illustrating an updating process of a cumulative function.
Figure 11G:
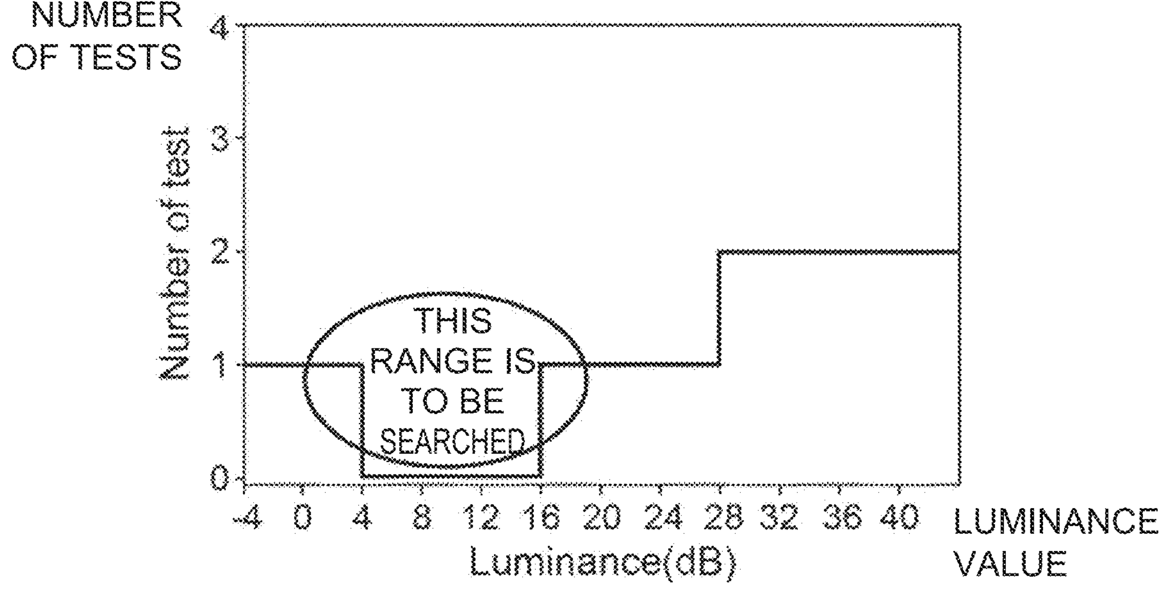
FIG. 11G is another diagram illustrating an updating process of a cumulative function.
Figure 11H:
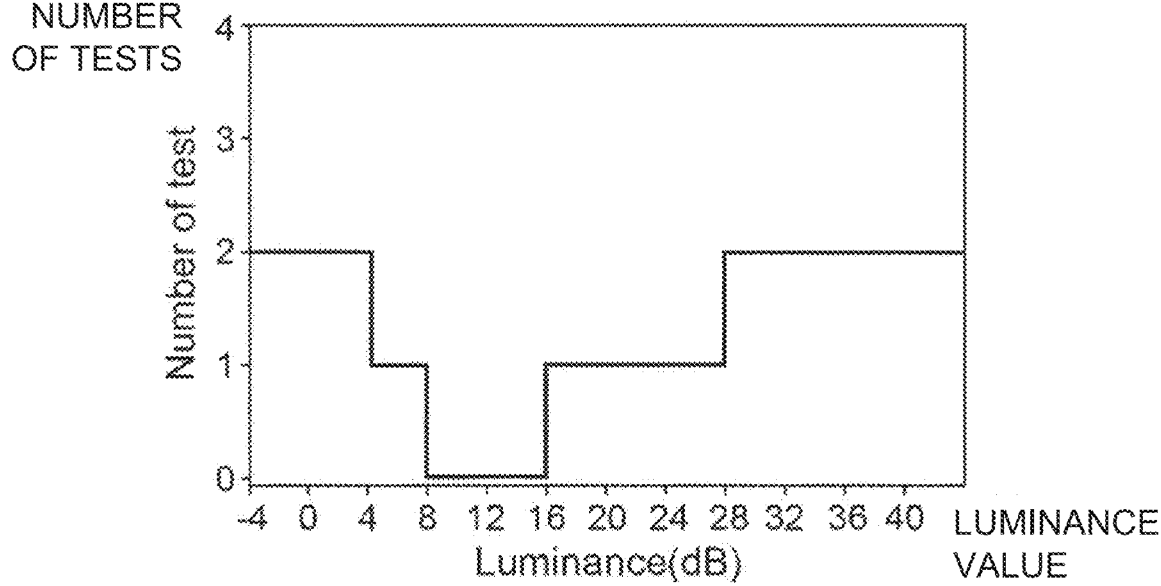
FIG. 11H is another diagram illustrating an updating process of a cumulative function.

Suppose that, for example, 16 dB is extracted from a range of luminance values in which the number of tests is less than 1 according to the cumulative function (see FIG. 11B) in step 122 during the repetition, and indicator light having a luminance value of 16 dB is presented as illustrated in FIG. 11D. Suppose that the subject does not recognize the indicator light having a luminance value of 16 dB. In this case, the test point selling unit 72 increases the number of tests for each luminance value in a range determined with 16 dB as a boundary (in a range of 16 dB or more), by a predetermined amount (for example, 1), for the above reason. As a result, the cumulative function is updated such that the number of tests for a luminance value in a range of from 16 dB to less than 28 dB is 1, and the number of tests for a luminance value in a range of 28 dB or more is 2 as illustrated in FIG. 11D. In this case, it is necessary to search (test) whether or not a range of luminance values smaller than 16 dB can be recognized as illustrated in FIG. 11E.

A range of luminance values that needs to be searched (tested) is narrowed by repeating the processes from step 120 to step 128, and updating the cumulative function as illustrated in FIGS. 11F, 11G, 11H, and 11I as described above. As a result, an upper limit value and a lower limit value of the range of luminance values that needs to be searched (tested) are determined, and the cumulative function having a downwardly projecting linear shape can be created.

Figure 11I:
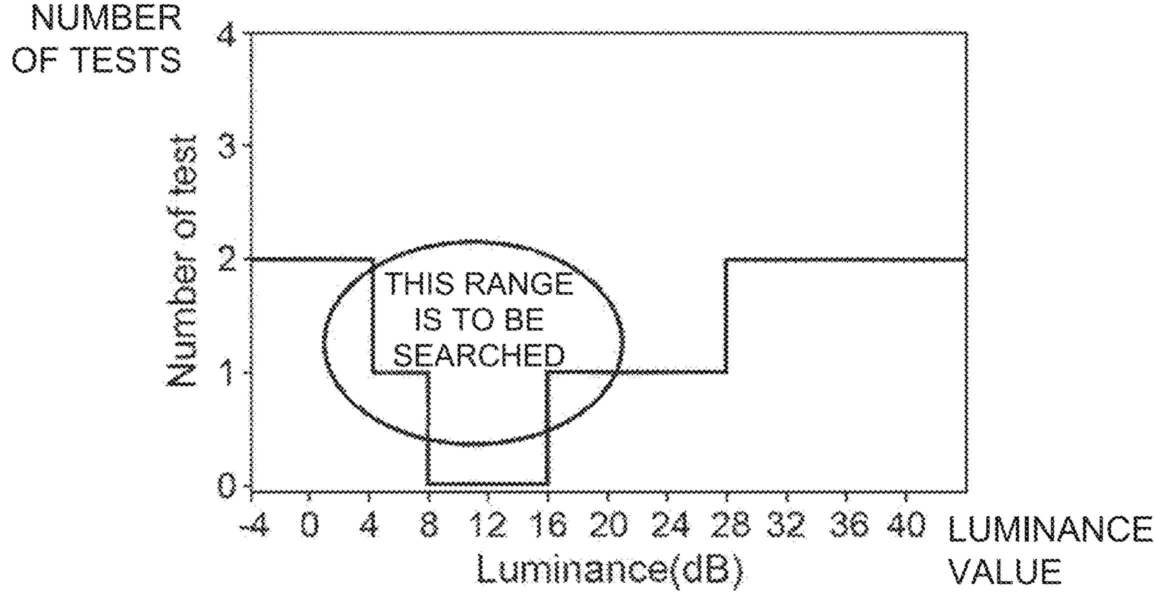
FIG. 11I is another diagram illustrating an updating process of a cumulative function.

In a case in which the cumulative function of the test point selected in step 116 is in a state illustrated in FIG. 11I, a subject's reaction is acquired by subsequently presenting indicator light having a luminance value of 12 dB to the test point selected in step 116. However, in a case in which the cumulative function of the test point selected in step 116 is in the state illustrated in FIG. 11I, the visual field sensitivity of the subject at this test point is expected to be a value around 12 dB. It is determined whether the visual field sensitivity of the test point selected in step 116 can be estimated in this manner.

The example described above with reference to FIGS. 11A to 11I is an example of a case in which there is no past data as described above. In a case in which it is determined in step 104 of FIG. 9 that the past data exists, a cumulative function and an estimated value of the visual field sensitivity exist for each test point of the test point set 200 corresponding to the patient ID. In a case in which the process in step 104 of FIG. 9 is executed in this case, it is determined as Yes in step 104. In step 122, either or both of the cumulative function and the estimated value of the visual field sensitivity for each test point of the test point set 200 in the past data are used. For example, in a case in which a luminance value having the smallest value of the cumulative function is 32 dB and the estimated value of the visual field sensitivity is 28 dB, 30 dB as an average value thereof is presented in a method of selecting a luminance value of indicator light to be presented.

In step 132, it is determined whether or not a determination condition is satisfied. The determination condition in step 132 is whether or not all the initial test points set in step 110 have been tested. In a case in which all the initial test points have been tested in step 132, the procedure proceeds to step 134. In a case in which not all the initial test points have been tested, the procedure proceeds to step 116, and the procedure from step 116 to step 130 is performed.

In step 134, test data obtained by the procedure up to step 132 is read. In step 136, the test point setting unit 72 performs data interpolation for estimating the entire visual field sensitivity, that is, the visual field sensitivity (estimated luminance value) for each test point of the test point set 200 on the basis of the cumulative function obtained for each test point in the test point set 200. In the present embodiment, data interpolation is performed independently in the upper area 202 and the lower area 204 as described above. In a case in which the visual field test area is divided into four areas as illustrated in FIG. 8C, data interpolation is performed independently in each of the four divided areas on the basis of test results in each of the four divided areas.

In the present embodiment, the test point setting unit 72 estimates the visual field sensitivity (estimated luminance value) for each test point of the test point set 200 including the initial test points. The test point setting unit 72 estimates an estimated luminance value of an untested point from an estimated luminance value of each tested point by using a stochastic process, and estimates reliability indicating the certainty of the estimated luminance value of the untested point that has been estimated.

In the present embodiment, the test point setting unit 72 numerically obtains the estimated luminance value of an untested point. The stochastic process in this case is referred to as "stochastic field". In the present embodiment, the test point setting unit 72 estimates the estimated luminance value of an untested point from the estimated luminance value of each tested point by using the stochastic process or the stochastic field, and estimates the reliability of the estimated luminance value of the untested point that has been estimated, by using the stochastic process or the stochastic field.

In the present embodiment, Gaussian process regression (GPR) is used as the stochastic process. In the technology of the disclosure, the stochastic process is not limited to the Gaussian process regression. Other examples of the stochastic process include t-process regression. In the present embodiment, data interpolation using the stochastic process is performed independently in the upper area 202 and the lower area 204, for example, as described above.

As described above, the reliability is numerical data indicating the certainty of the estimated luminance value of the untested point that has been estimated. Specifically, the reliability is numerical data indicating a possible range of the visual field sensitivity of the untested point centered on the estimated luminance value of the untested point that has been estimated.

Figure 10:
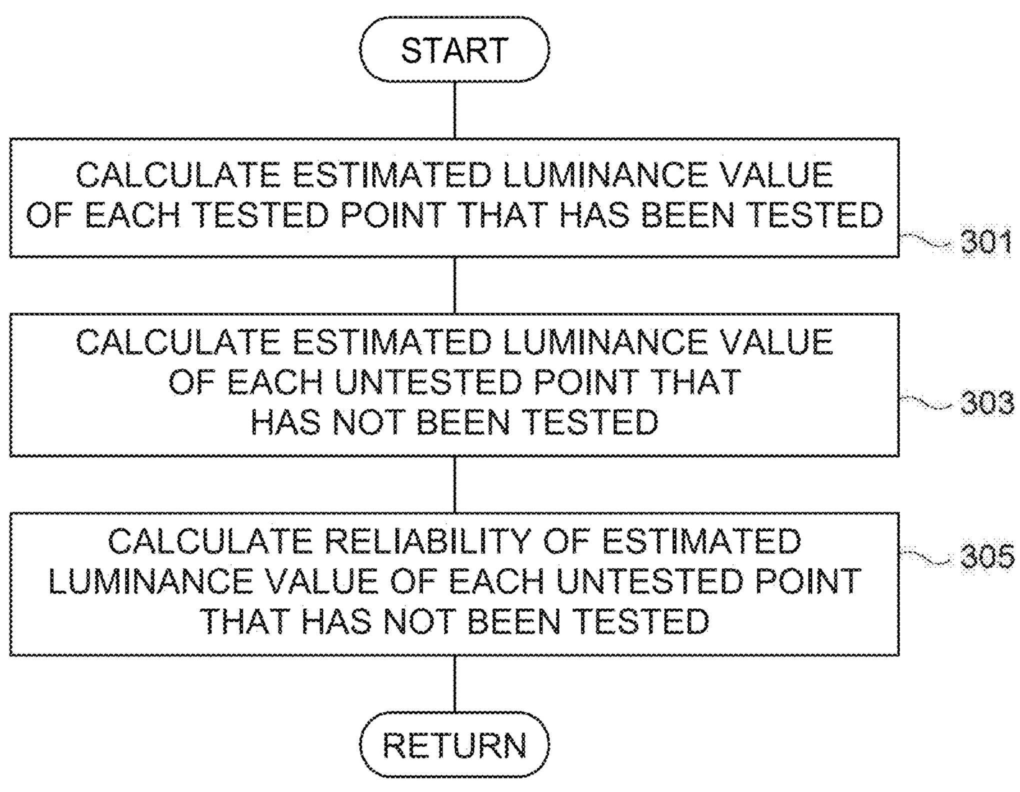
FIG. 10 is a flowchart of a process of estimating and interpolating visual field sensitivities of all test points in step 136 of FIG. 9.
Figure 12:
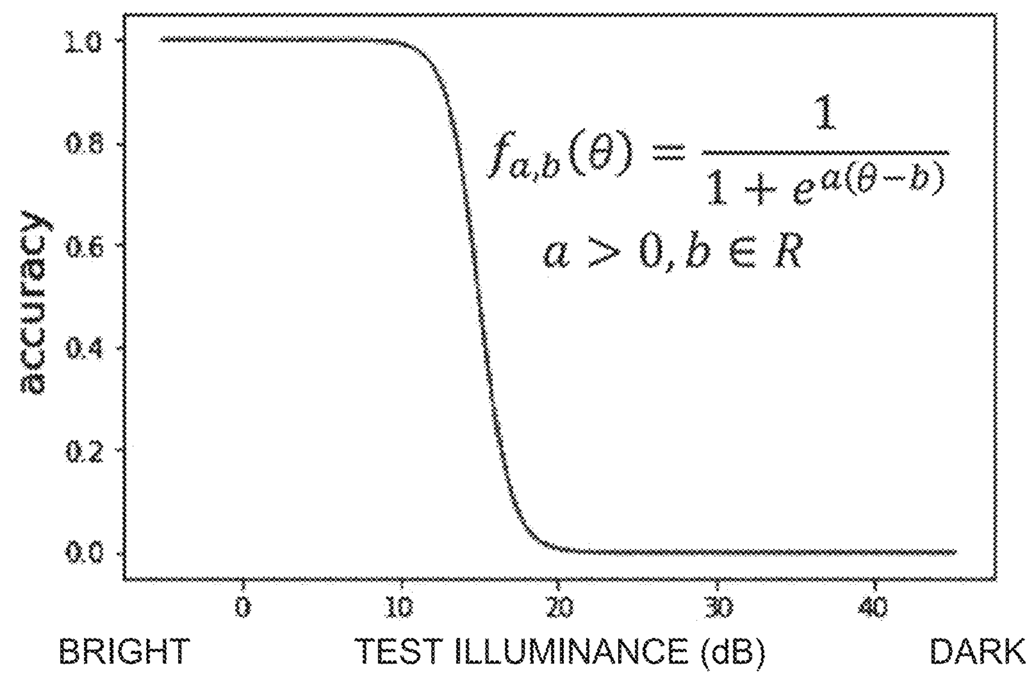
FIG. 12 is an explanatory view illustrating a luminance value-correct answer rate curve indicating a relationship between a luminance value and a probability $f_{a,b}(\theta)$ with which indicator light of the luminance value is recognized at a test point of the optic nerve of the eye to be tested 12 of a subject.

FIG. 10 illustrates a flowchart of the process of estimating and interpolating the visual field sensitivities of all the test points in step 136 of FIG. 9. As illustrated in FIG. 10, the test point setting unit 72 calculates the estimated luminance value of each tested point in step 301. Specifically, first, the test point setting unit 72 uses a luminance value-correct answer rate curve illustrated in FIG. 12 indicating a relationship between a luminance value and a probability $f_{a,b}(\theta)$ with which indicator light of the luminance value is recognized at a test point of the optic nerve of the eye to be tested 12 of a subject in order to calculate the estimated luminance value (visual field sensitivity) of each tested point. The luminance value-correct answer rate curve is defined by the following formula. In the following formula, θ is a luminance value used in each test at a test point.

$$f_{a,b}(\theta) = \frac{1}{1 + e^{a(\theta - b)}} \quad \text{[Formula 1]}$$

As described below, a is a constant greater than 0, and b is a value included in R (R is a set of all real numbers).

$$a > 0, b \in R \quad \text{[Formula 2]}$$

The test point setting unit 72 obtains a likelihood L(a,b) of each tested point from the following formula by using the formula indicating the curve described above. More specifically, for example, in a case in which indicator light has a luminance value of 20 dB and a subject's reaction that the indicator light is recognized (Yes) is obtained at a certain tested point in a first test, the test point setting unit 72 uses a probability $f_{a,b}(20)$. In a case in which indicator light has a luminance value of 24 dB and a subject's reaction that the indicator light is not recognized (No) is obtained in a second test, the test point setting unit 72 uses $(1-f_a(24))$. In a case in which indicator light has a luminance value of 16 dB and a subject's reaction that the indicator light is recognized (Yes) is obtained in a third test, the test point setting unit 72 uses a probability $f_{a,b}(16)$. The test point setting unit 72 obtains b with which the likelihood L(a,b) becomes maximum for each tested point by using the product of values corresponding to the results of all the tests as described above.

$$L(a,b) = f_{a,b}(20)\,(1 - f_{a,b}(24)) f_{a,b}(16) \quad \text{[Formula 3]}$$

The estimated luminance value of each tested point uses b obtained for each tested point. For example, 21 dB is calculated as the estimated luminance value at a tested point ($x_2$), 19.6 dB is calculated as the estimated luminance value at a tested point ($x_3$), and 31.5 dB is calculated as the estimated luminance value at a tested point ($x_5$).

In step 303, the test point setting unit 72 calculates the estimated luminance value of each untested point that has not been tested, by using the Gaussian process regression. Specifically, the test point setting unit 72 calculates, for each untested point, an estimated luminance value E[X(x*)|D] from the following formula by using the estimated luminance value of each tested point.

$$\mathbb{E}[X(x^*) \mid \mathcal{D}] = k_{*\mathcal{D}}^T K_{\mathcal{D}}^{-1} y_{\mathcal{D}} \quad \text{[Formula 4]}$$

$$k_{*\mathcal{D}} = \begin{pmatrix} K(x_1, x^*) \\ K(x_2, x^*) \\ \vdots \\ K(x_N, x^*) \end{pmatrix} \quad \text{[Formula 5]}$$

$$K_{\mathcal{D}} = \begin{pmatrix} K(x_1, x_1) & K(x_1, x_2) & \dots & K(x_1, x_N) \\ K(x_2, x_1) & K(x_2, x_2) & \dots & K(x_2, x_N) \\ \vdots & \vdots & \ddots & \vdots \\ K(x_N, x_1) & K(x_N, x_2) & \dots & K(x_N, x_N) \end{pmatrix} \quad \text{[Formula 6]}$$

$$y_{\mathcal{D}} = \begin{pmatrix} y_1 \\ y_2 \\ \vdots \\ y_N \end{pmatrix} \quad \text{[Formula 7]}$$

$k^*_D$ in Formula 4 and K(x,x') of $K_D$ in Formula 5 are the following Gaussian radial basis function kernels (RBF kernels). In the following formula. $\theta_1$ and $\theta_2$ are real numbers.

$$K(x, x') = \theta_1 \exp\left(-\frac{|x - x'|^2}{\theta_2}\right) \quad \text{[Formula 8]}$$

x of K(x,x') represents each of $x_1, x_2, \dots X_N$, and each of $x_1, x_2, \dots X_N$ is XY coordinates of a position of a tested point.

x' of K(x,x') is XY coordinates of each untested point x*.

Each of y1, y2, . . . $Y_N$ of $Y_D$ is an estimated luminance value of a tested point.

The estimated luminance value E[X(x*)|D] of each untested point obtained as described above is an average value of luminance values estimated for each untested point from the estimated luminance value of each tested point.

In step 305, the test point setting unit 72 calculates a variance V[X(x*)|D] from the following formula as the reliability of the estimated luminance value of each untested point that has not been tested, by using the Gaussian process regression.

$$\mathbb{V}_{[X(x^*)|\mathcal{D}]} = k_{**} - k_{*\mathcal{D}}^T K_{\mathcal{D}}^{-1} k_{*\mathcal{D}} \quad \text{[Formula 9]}$$

$k_{**}$ is as follows.

$$k_{**} = K(x^*, x^*) \quad \text{[Formula 10]}$$

After the process in step 305 ends, the process in step 136 of FIG. 9 ends.

Figure 13:
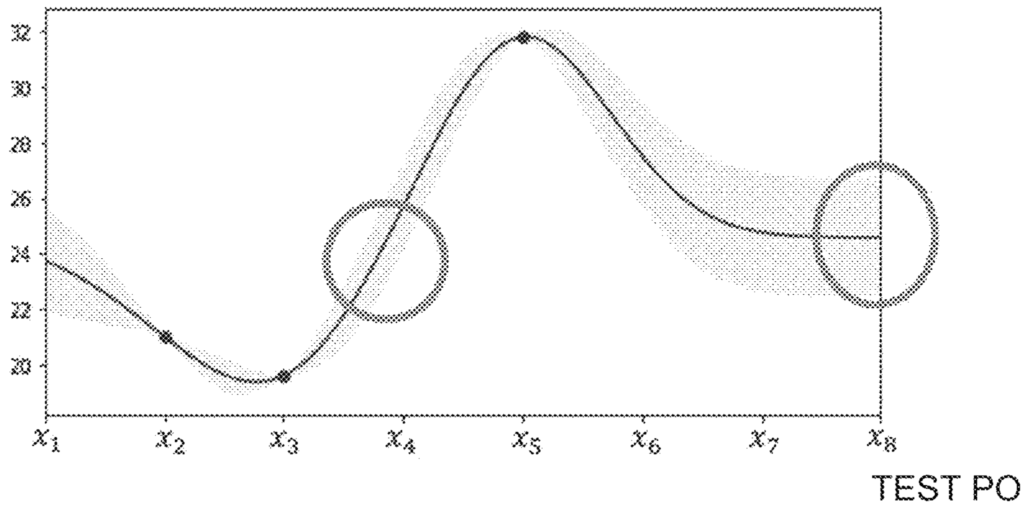
FIG. 13 is a schematic view illustrating a relationship between a test point (including an untested point and a tested point) and an estimated luminance value of each test point.

FIG. 13 is a diagram illustrating a relationship between a test point (including an untested point and a tested point) and the estimated luminance value of each test point. As a result of the ending of the process in step 136 of FIG. 9, the estimated luminance value of each tested point ($x_2$, $x_3$, $x_5$, . . . ) is obtained, and the estimated luminance values of the untested points ($x_1$, $x_4$, $x_6$, $x_7$, $x_8$, . . . ) and the reliability thereof are obtained as illustrated in FIG. 13, for example. In FIG. 13, a colored area existing around a curve indicates an error range, in which the reliability of the estimated luminance value is higher as the colored area has a smaller width, and the reliability of the estimated luminance value is lower as the colored area has a larger width.

For example, the untested point ($x_4$) is adjacent to the tested points ($x_3$, $x_5$) and relatively close to the tested points ($x_3$, $x_5$) as illustrated in FIG. 13. However, the untested point ($x_8$) is relatively far from the tested point ($x_5$). Therefore, the error range of the estimated luminance value of the untested point ($x_4$) is relatively small and the reliability has a high value, whereas the error range of the estimated luminance value of the untested point ($x_8$) is relatively large and the reliability is low.

In step 138, the test point setting unit 72 determines whether or not an additional test is necessary. The necessity of an additional test is determined on the basis of the error range of the estimated luminance value. In a case in which there is a test point the error range of which exceeds a predetermined range among the test points for which the estimated luminance value has been calculated, it is determined that the additional test is necessary in step 138. The predetermined range in step 138 is specifically determined through a test for calculating the estimated luminance value.

In a case in which it is determined in step 138 that no additional test is required, the process ends. In a case in which the additional test is required, the procedure proceeds to step 140.

In step 140, the test point setting unit 72 sets a set of additional test points. In the present embodiment, a case of the subject is estimated on the basis of test results of the initial test points, and additional test points are set according to the estimated case. The case estimation and the setting of additional test points may be performed using, for example, the control device 10 that has performed machine learning by a recurrent neural network (RNN) or the like. In the machine learning by the RNN or the like, the control device 10 is trained using test results related to respective cases as training data.

Figure 14A:
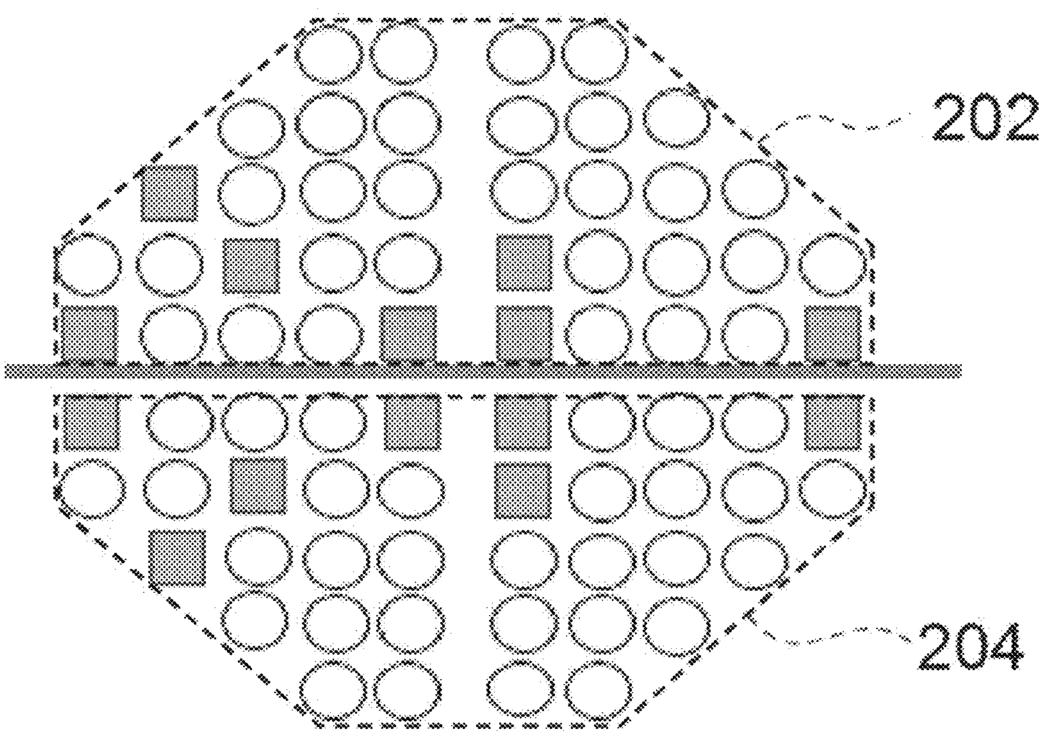
FIG. 14A is a schematic view illustrating an example of test results of respective test points in a case in which there is no abnormality.
Figure 14B:
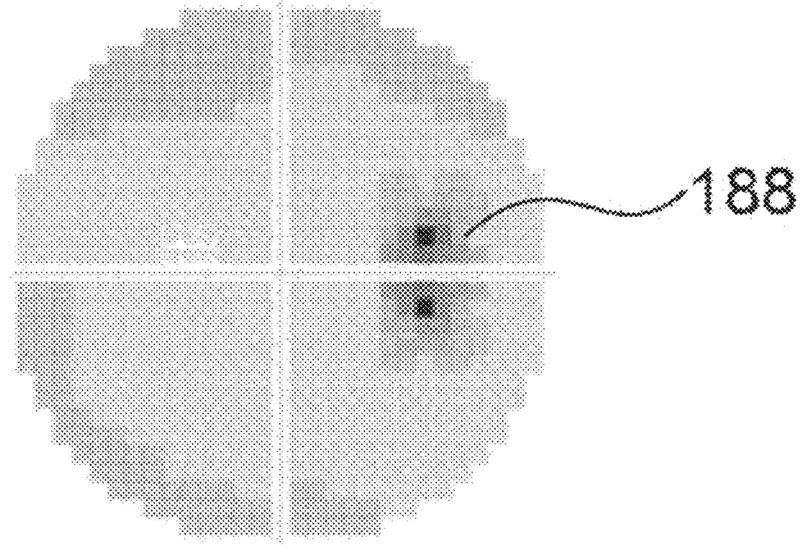
FIG. 14B is a schematic view illustrating an example of a visual field sensitivity map in the case of no abnormality.

FIG. 14A is a schematic view illustrating an example of test results of respective test points in a case in which there is no abnormality. In a case in which all of initial test points indicated by squares in FIG. 14A are normal, it is estimated that only the dark spot 188 corresponding to the optic nerve head 184 that is the blind spot 186 exists in a visual field sensitivity map illustrated in FIG. 14B. The same number of additional test points indicated by pentagons are set in an area where the initial test points of the upper area 202 are sparse and an area where the initial test points of the lower area 204 are sparse as illustrated in FIG. 14C.

Figure 15A:
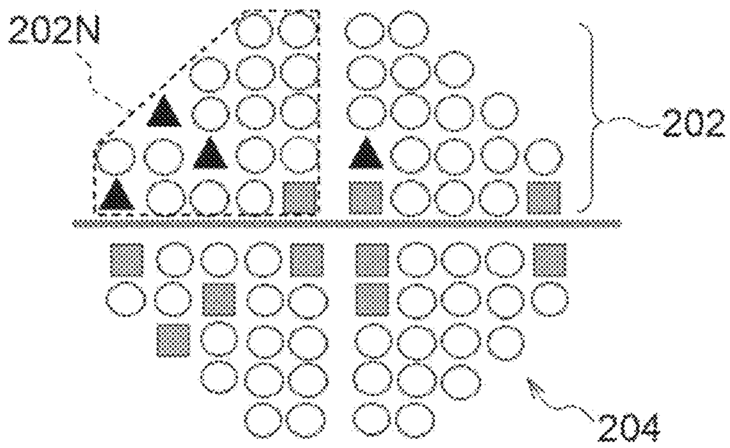
FIG. 15A is a schematic view illustrating an example of test results of respective test points in a case in which the upper area 202 has a nasal breakthrough.

FIG. 15A is a schematic view illustrating an example of test results of respective test points in a case in which the upper area 202 has a nasal breakthrough. In a case in which visual field sensitivity defective points indicated by triangles are noticeable in a nasal area 202N of the upper area 202 as illustrated in FIG. 15A, there is a possibility that the upper area 202 has a nasal breakthrough.

Figure 15B:
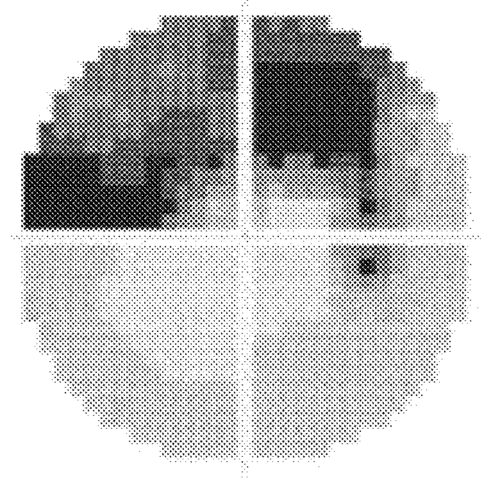
FIG. 15B is a schematic view illustrating an example of a visual field sensitivity map in the case of the upper area 202 having a nasal breakthrough.
Figure 15C:
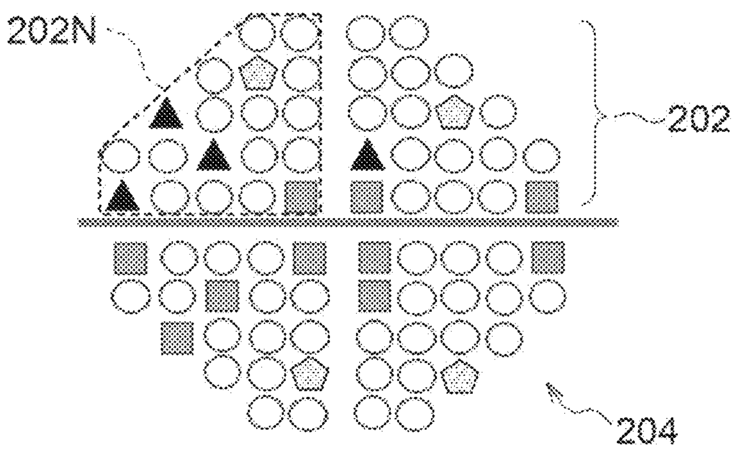
FIG. 15C is a schematic view illustrating setting of additional test points in the case of the upper area 202 having a nasal breakthrough.

FIG. 15B is a schematic view illustrating an example of a visual field sensitivity map in the case of the upper area 202 having a nasal breakthrough. In a case in which there is a possibility that the upper area 202 has a nasal breakthrough in step 140, it is estimated that the visual field sensitivity defective points are distributed as illustrated in FIG. 15B. The same number of additional test points indicated by pentagons are set in an area where the initial test points of the upper area 202 are sparse and an area where the initial test points of the lower area. 204 are sparse as illustrated in FIG. 15C.

Figure 16A:
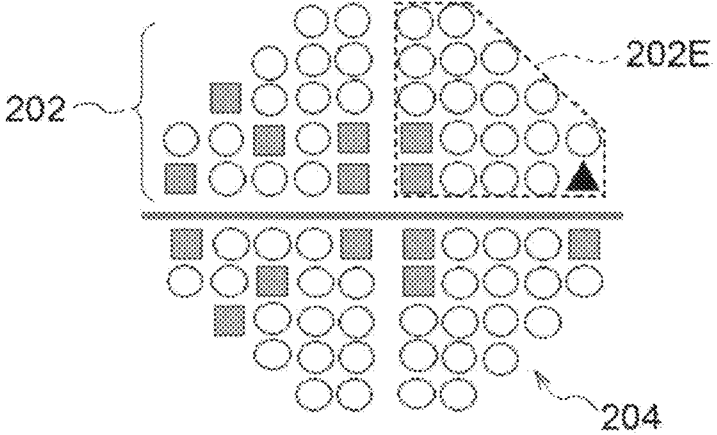
FIG. 16A is a schematic view illustrating an example of test results of respective test points in a case in which the upper area 202 has a temporal wedge defect.

FIG. 16A is a schematic view illustrating an example of test results of respective test points in a case in which the upper area 202 has a temporal wedge defect. In a case in which visual field sensitivity defective points indicated by triangles are noticeable in a temporal area 202E of the upper area 202 as illustrated in FIG. 16A, there is a possibility that the upper area 202 has a temporal wedge defect.

Figure 16B:
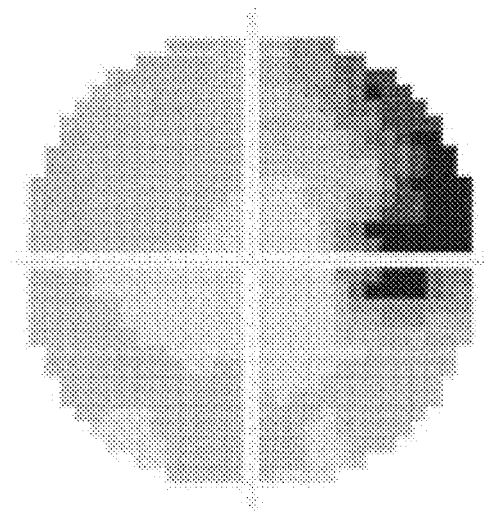
FIG. 16B is a schematic view illustrating an example of a visual field sensitivity map in the case of the upper area 202 having a temporal wedge detect.
Figure 16C:
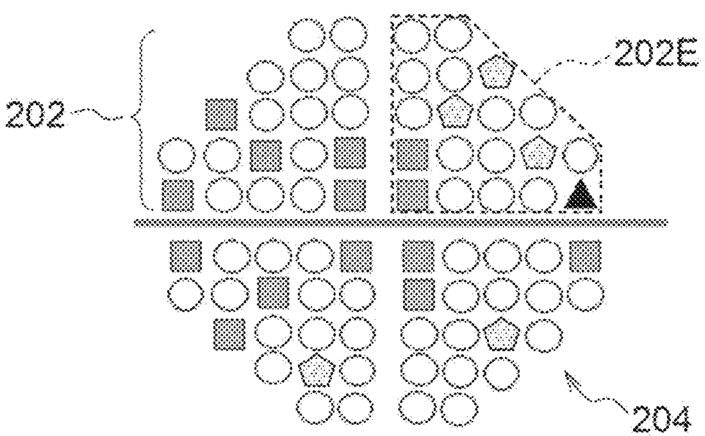
FIG. 16C is a schematic view illustrating an example of setting additional test points in the case of the upper area 202 having a temporal wedge defect.

FIG. 16B is a schematic view illustrating an example of a visual field sensitivity map in the case of the upper area 202 having a temporal wedge defect. In a case in which there is a possibility that the upper area 202 has a temporal wedge defect in step 140, it is estimated that the visual field sensitivity defective points are distributed as illustrated in FIG. 16B. Additional test points are set in each of an area where the initial test points of the upper area 202 are sparse and an area where the initial test points of the lower area 204 are sparse as illustrated in FIG. 16C. Here, the test point setting unit 72 preferentially sets additional test points indicated by pentagons in a temporal area 202E of the upper area 202 suspected of having a disease.

Figure 17A:
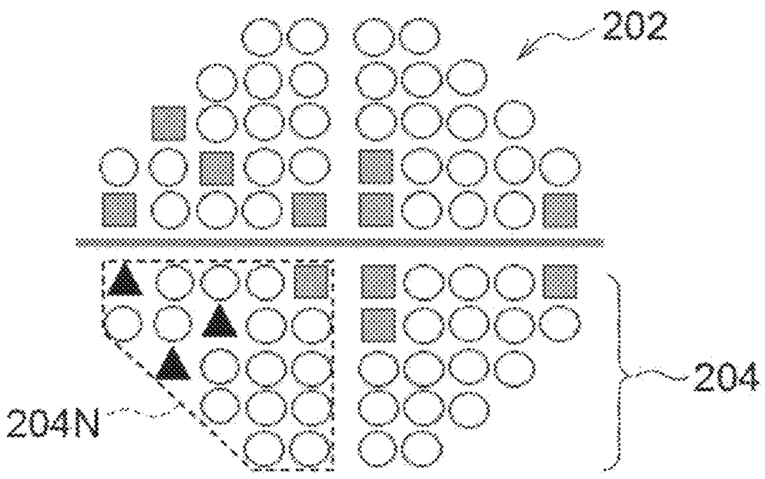
FIG. 17A is a schematic view illustrating an example of test results of respective test points in a case in which the lower area 204 has a nasal step.

FIG. 17A is a schematic view illustrating an example of test results of respective test points in the case of a nasal step. In a case in which visual field sensitivity defective points indicated by triangles are noticeable in a nasal area 204N of the lower area 204 as illustrated in FIG. 17A, there is a possibility that the lower area 204 has a nasal step.

Figure 17B:
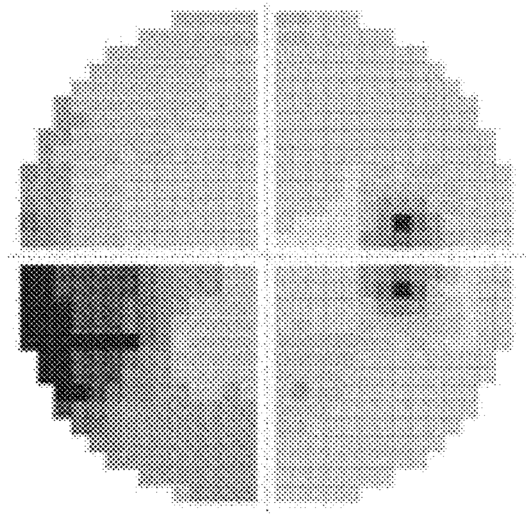
FIG. 17B is a schematic view illustrating an example of a visual field sensitivity map in the case of the lower area 204 having a nasal step.
Figure 17C:
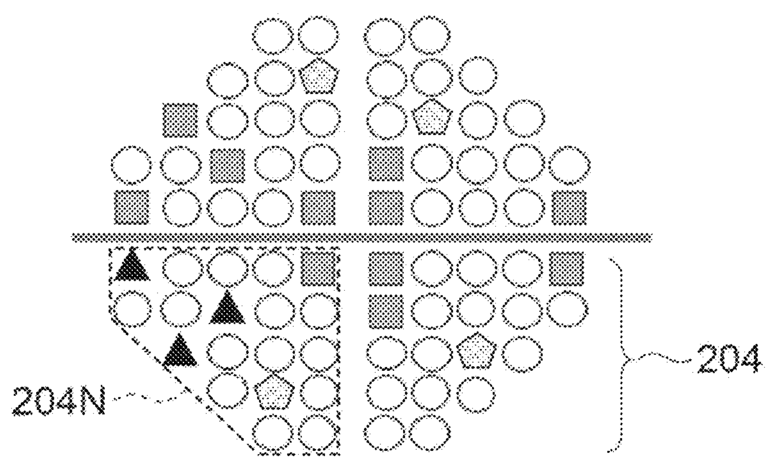
FIG. 17C is a schematic view illustrating an example of setting additional test points in the case of the lower area 204 having a nasal step.

FIG. 17B is a schematic view illustrating an example of a visual field sensitivity map in the case of the lower area 204 having a nasal step. In a case in which there is a possibility that the lower area 204 has a nasal step in step 140, it is estimated that the visual field sensitivity defective points are distributed as illustrated in FIG. 17B. Additional test points indicated by pentagons are set in each of an area where the initial test points of the upper area 202 are sparse and an area where the initial test points of the lower area 204 are sparse as illustrated in FIG. 17C. Diseases such as an arcuate scotoma, a paracentral scotoma, an altitudinal hemianopsia-like visual field, and a central residual visual field may also be determined in addition to the nasal breakthrough, the temporal wedge defect, and the nasal step described above, and additional test points may be set according to the determined disease.

In step 142, the test point setting unit 72 selects luminance values of indicator light to be presented to the additional test points set in step 140. In step 142, the luminance values may be, for example, selected randomly, may be selected by an operator, or may be automatically selected on the basis of past data.

In step 144, one test point is selected from the set of additional test points set in step 140. The test point to be selected may be selected randomly from the set of additional test points, may be selected by an operator, or may be automatically selected on the basis of past data.

In step 146, the cumulative number of tests of the test point selected in step 144 is acquired. The cumulative number of tests can be extracted from the cumulative function described above, but may be held as data independent of the cumulative function as the cumulative number of tests.

In step 148, it is determined whether or not the cumulative number of tests is 1 or more. In a case in which the cumulative number of tests is 1 or more in step 148, the procedure proceeds to step 150. In a case in which the cumulative number of tests is less than 1, the procedure proceeds to step 152.

In step 150, indicator light having a luminance value based on the cumulative function is presented to the test point selected in step 144. The test point setting unit 72 sets the luminance value of the presented indicator light from a range of luminance values extracted from the cumulative function. In the technology of the disclosure, the luminance value of the presented indicator light may be randomly extracted and set, or an optionally determined value may be extracted and set, from the range of the extracted luminance values. For example, the test point setting unit 72 may extract, from this range, a median value, a value of ¾, or the like in the range as the luminance value of the presented indicator light. Next, the test point setting unit 72 controls the projector such that the indicator light of the extracted luminance value is incident on the test point selected in step 144.

In step 152, indicator light of the initial luminance value set in step 142 is presented to the subject.

In step 154, the test point setting unit 72 acquires a reaction of the subject. In a case in which the subject recognizes the indicator light presented in step 150 or step 152, the subject tunes on the switch of the response unit 60. As a result, a recognition signal is transmitted to the control device 10. In a case in which the subject does not recognize the indicator light when presented with the indicator light, the subject does not turn on the switch of the response unit 60. The test point setting unit 72 determines whether or not the subject recognizes the indicator light on the basis of whether or not the recognition signal is transmitted before the elapse of a predetermined time from the presentation of the indicator light. For example, in a case in which the recognition signal is transmitted before the elapse of a predetermined time from the presentation of the indicator light, the test point setting unit 72 acquires a reaction of the subject that the subject recognizes the indicator light. In a case in which the recognition signal is not transmitted even after the lapse of the predetermined time, the test point setting unit 72 acquires a reaction of the subject that the subject does not recognize the indicator. The test point setting unit 72 stores the reaction of the subject acquired in step 154 in the external storage device 40.

In step 156, the test point setting unit 72 updates the cumulative function. In the present embodiment, the processes from step 144 to step 156 are repeated, and the cumulative function updating process in step 156 is also repeated. The cumulative number of test is also updated. By repeating the processes from step 144 to step 156, indicator light having different luminance values is presented a plurality of times to each test point belonging to the set of additional test points set in step 140, and the reaction of the subject to each indicator light is obtained. Therefore, the cumulative function corresponding to each test point is updated on the basis of the reaction of the subject in each presentation similarly to step 128.

In step 158, the test point setting unit 72 determines whether or not the visual field sensitivity of the test point selected in step 144 can be estimated with sufficient accuracy. In the present embodiment, it is determined whether or not the cumulative function forms a downwardly projecting linear shape as in FIG. 11I, and the luminance of indicator light that can be recognized by the subject can be estimated similarly to step 130.

In step 160, it is determined whether or not a determination condition is satisfied. The determination condition in step 160 is whether or not all the additional test points set in step 140 have been tested. In a case in which all the additional test points have been tested in step 160, the procedure proceeds to step 162. In a case in which not all the additional test points have been tested, the procedure proceeds to step 144, and the procedure from step 144 to step 158 is performed.

In step 162, test data obtained by the procedure up to step 160 is read. In step 164, the test point setting unit 72 performs data interpolation for estimating the entire visual field sensitivity, that is, the visual field sensitivity (estimated luminance value) for each test point of the test point set 200 on the basis of the cumulative function obtained for each test point in the test point set 200 similarly to step 136.

In step 166, the image processing unit 74 creates screen data for visualizing the respective cumulative functions of each tested point and each additional test point, if any, the estimated luminance value of each test point of the entire test point set, and the reliability of the estimated luminance values of the untested points.

Specifically, a first example of the screen data is a graph illustrating the estimated luminance value of each test point of the entire test point set as illustrated in FIG. 18A.

A second example is a graph in which the reliability of the estimated luminance values of the untested points is added to the graph illustrating the estimated luminance value of each test point of the entire test point set, with the visual field sensitivity as the center, as illustrated in FIG. 18B.

Figure 19:
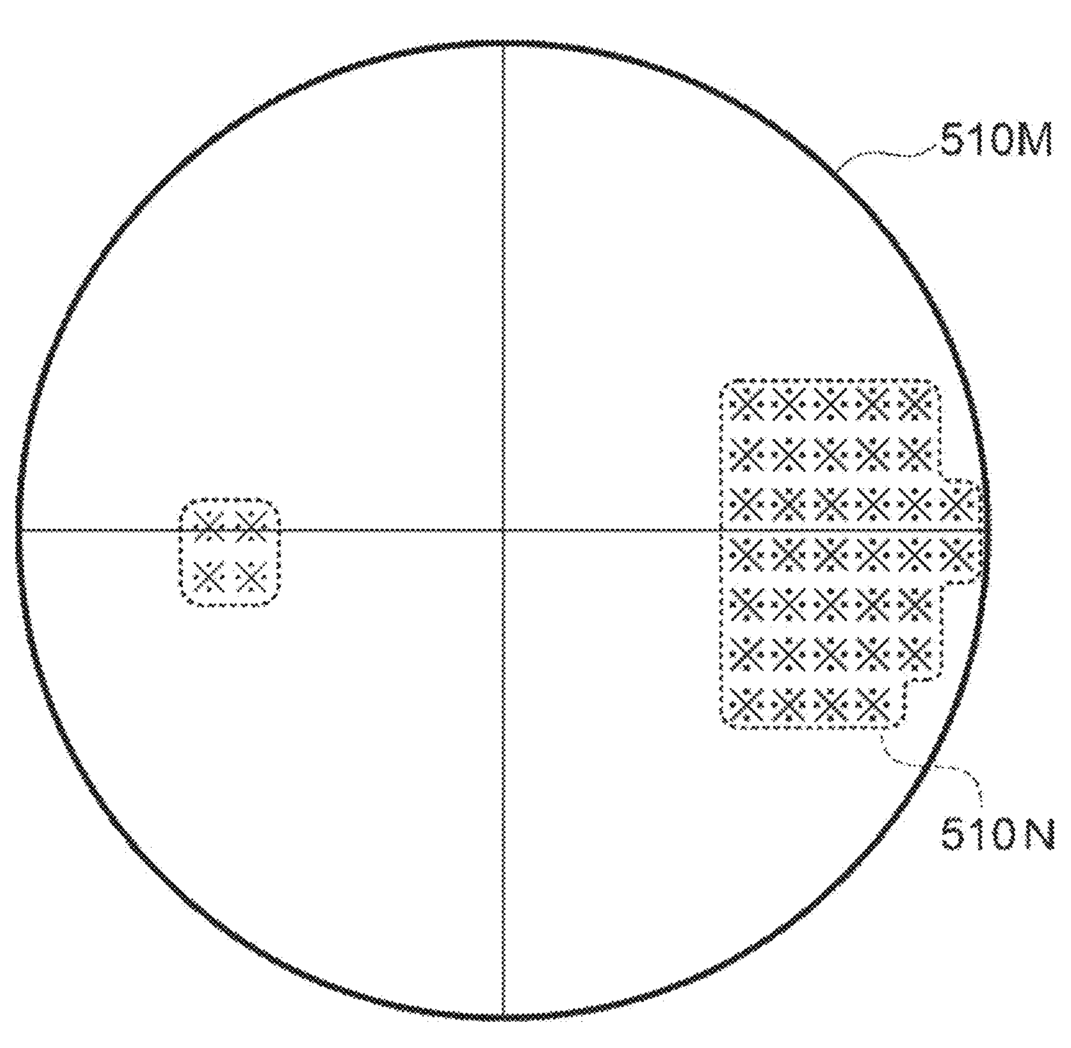
FIG. 19 is a diagram illustrating a visual field sensitivity map 510M.

A third example is a visual field sensitivity map as illustrated in FIG. 19. The visual field sensitivity map is an example of a method of displaying a visual field sensitivity distribution. The visual field sensitivity map displays a distribution of visual field sensitivity data of a plurality of test points included in a test point set. The visual field sensitivity map may be generated for the entire test point set, or may be generated for some of the test point set. The visual field sensitivity map also includes reliability data. Specifically, a visual field sensitivity map 5101 is data of a map screen in which * is attached to a test point the visual field sensitivity of which is less than a predetermined value (dB) in an image simulating the fundus of the eye to be tested 12 as illustrated in FIG. 19. The visual field sensitivity map 510M is screen data capable of displaying, with a dotted line, a range 510N of test points the reliability of which has a predetermined value or larger. The visual field sensitivity map 510M may also be screen data capable of displaying the reliability of the estimated luminance value of an untested point in a case in which, for example, a cursor is positioned at the untested point while displaying the untested points in a color different from colors of the tested points and the additional test points in each test point of the entire test point set, for example.

In the present embodiment, the range of luminance values that needs to be searched (tested) is gradually narrowed by updating the cumulative function for each test point in the test point set 200 as described above. As a result, the visual field test can be completed in a shorter time than in a case in which the luminance value of indicator light is randomly set. Hereinafter, the effectiveness of the present embodiment using the cumulative function will be described with reference to FIGS. 20A to 21C. In each of FIGS. 20A to 21C, the horizontal axis represents the number of tests, and the vertical axis represents a difference between a correct sensitivity value and an estimated sensitivity. On the vertical axis, 0 means that there is no difference between the correct value and the estimated value, and the estimated value has favorable accuracy.

Figure 20A:
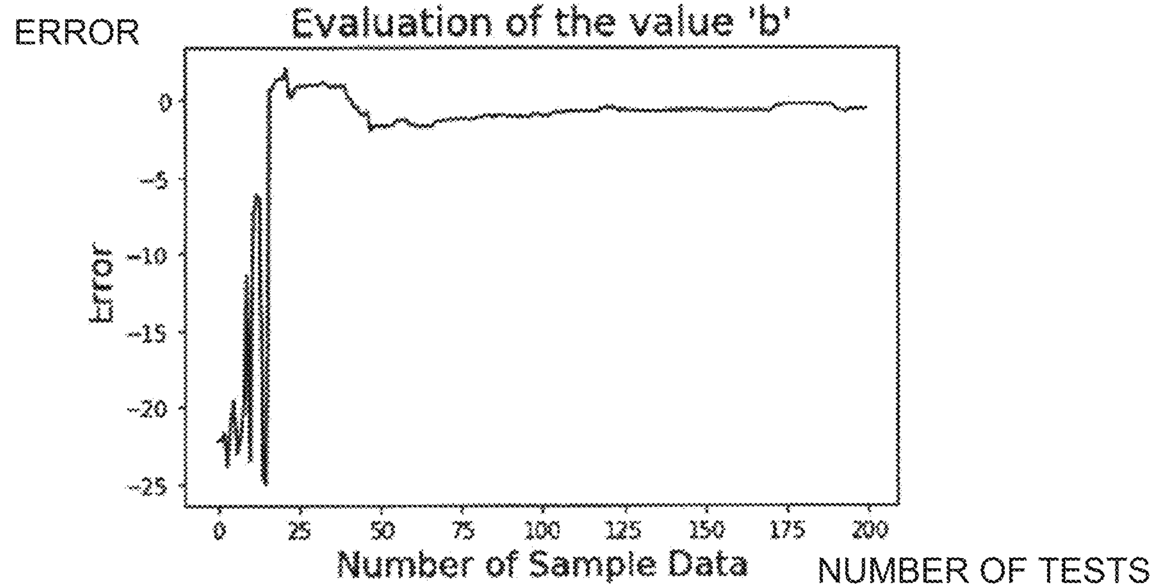
FIG. 20A is a diagram illustrating a relationship between the number of tests and a difference between a correct sensitivity value and an estimated sensitivity in the prior art.
Figure 20B:
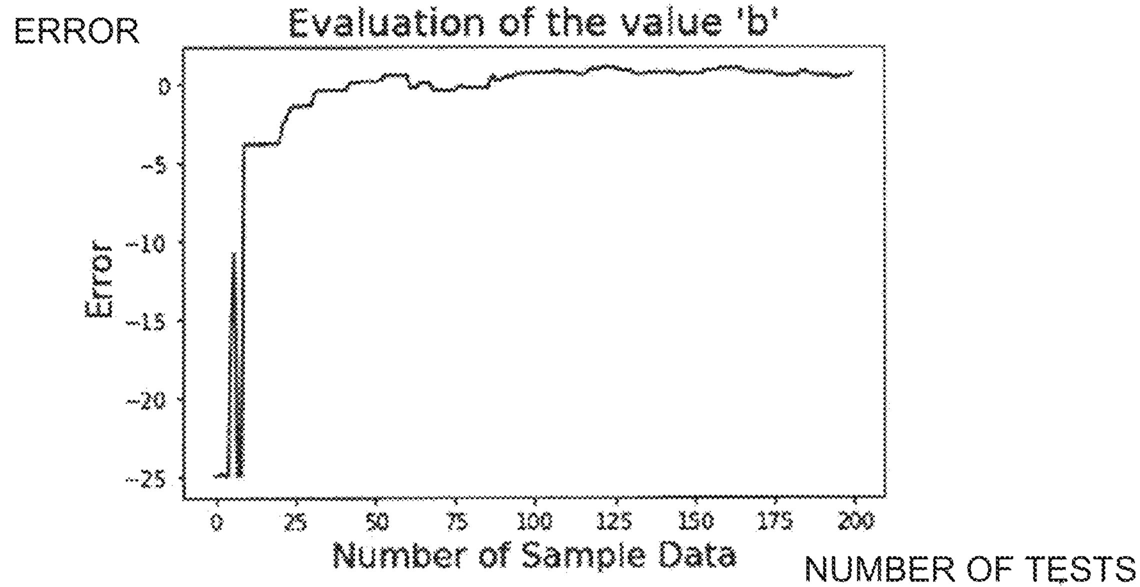
FIG. 20B is another diagram illustrating a relationship between the number of tests and a difference between a correct sensitivity value and an estimated sensitivity in the prior art.
Figure 20C:
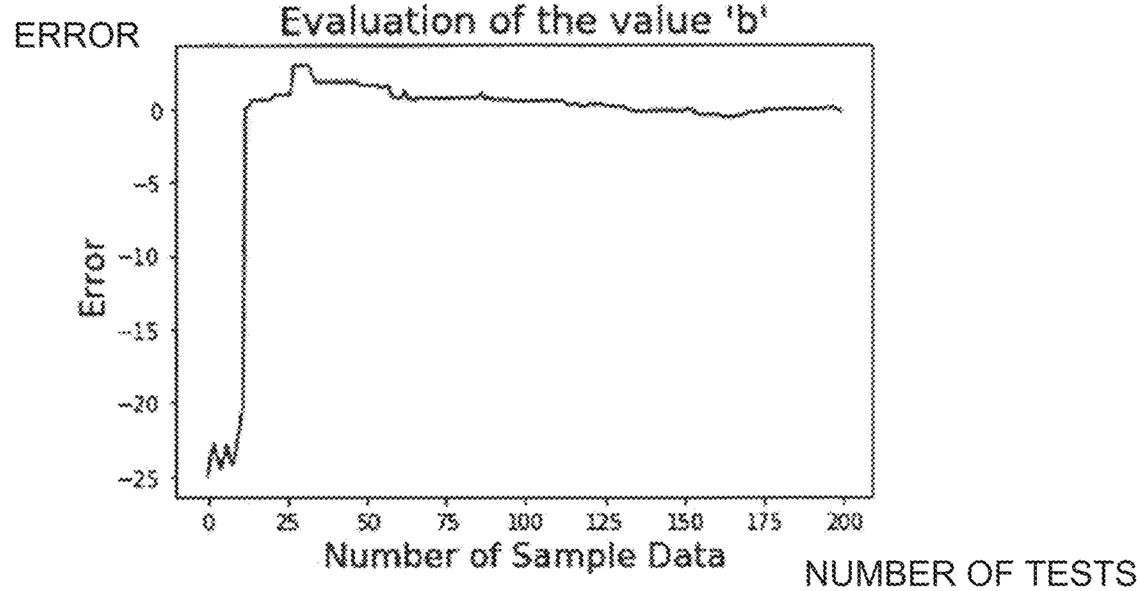
FIG. 20C is another diagram illustrating a relationship between the number of tests and a difference between a correct sensitivity value and an estimated sensitivity in the prior art.
Figure 21A:
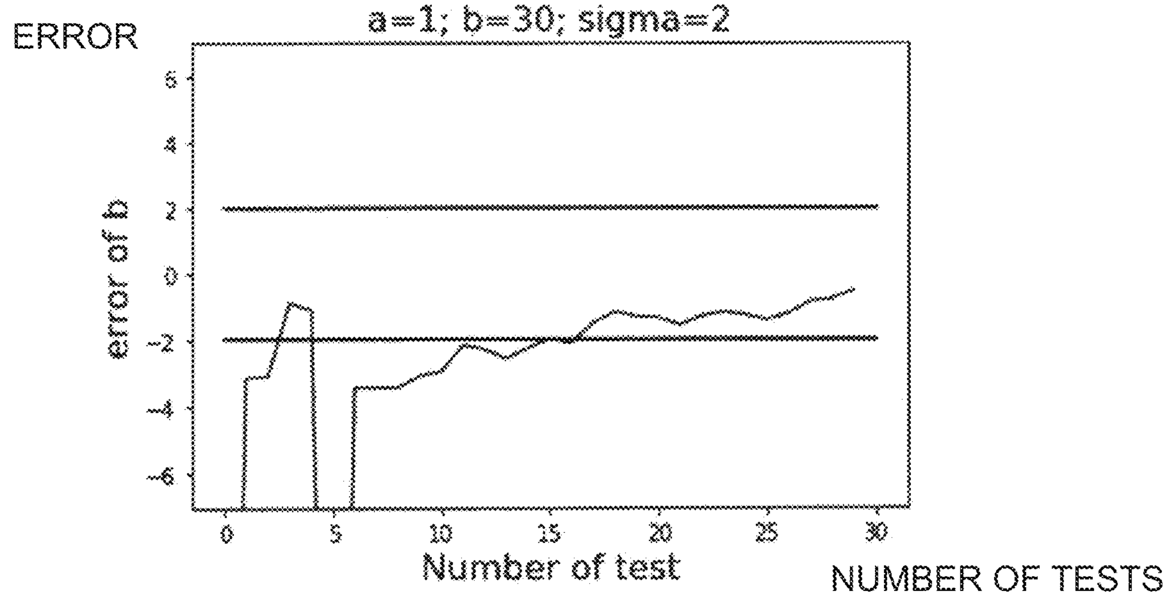
FIG. 21A is a diagram illustrating a relationship between the number of tests and a difference between a correct sensitivity value and an estimated sensitivity in the present embodiment.
Figure 21B:
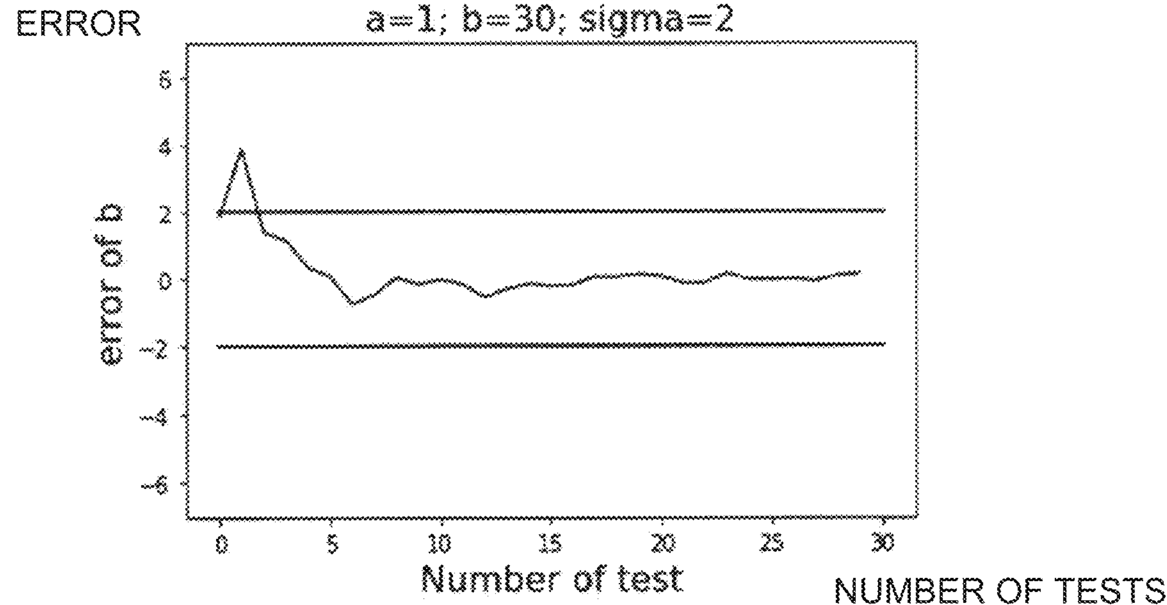
FIG. 21B is another diagram illustrating a relationship between the number of tests and a difference between a correct sensitivity value and an estimated sensitivity in the present embodiment.
Figure 21C:
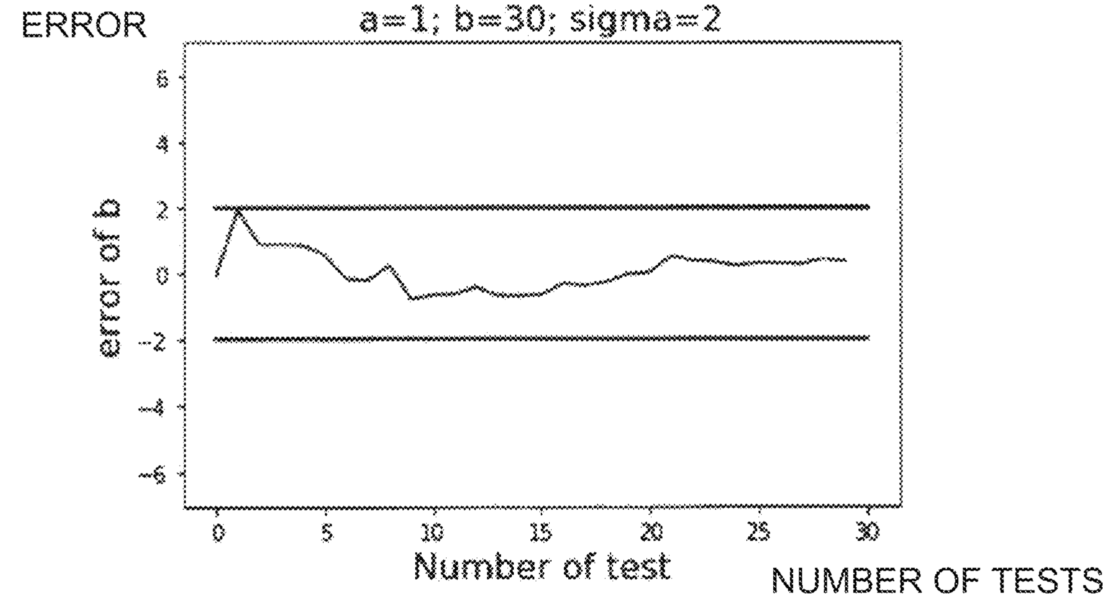
FIG. 21C is another diagram illustrating a relationship between the number of tests and a difference between a correct sensitivity value and an estimated sensitivity in the present embodiment.

FIGS. 20A to 20C illustrate the number of tests necessary for ensuring sufficient accuracy in visual field test results in a case in which light intensity is randomly selected, at three different points of the optic nerve of the fundus of an eye to be tested. FIGS. 21A to 21C illustrate the number of tests necessary for ensuring sufficient accuracy in a case in which the method of the present embodiment is applied, at three different points of the optic nerve of the fundus of an eye to be tested.

In the case of randomly selecting the luminance value (FIGS. 20A to 20C), the test needs to be performed 70 to 80 times. In the case of selecting the luminance value by the method of the present embodiment (FIGS. 21A to 21C), the test needs to be performed 3 to 15 times. Therefore, it can be understood that the method of the present embodiment contributes to reduction of the number of tests.

Figure 22:
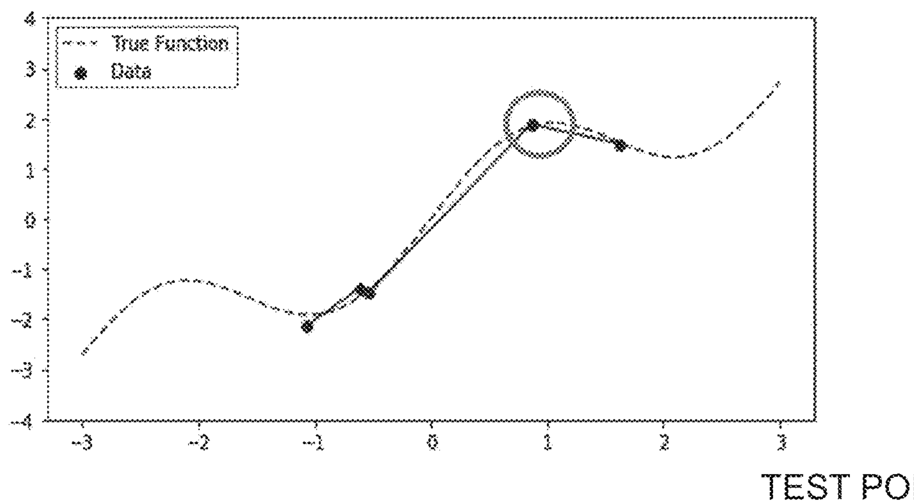
FIG. 22 is a diagram illustrating a method of interpolating an estimated luminance value of an untested point.

The reliability of an interpolated value is not considered in the case of a method of linearly interpolating the estimated luminance value of an untested point as illustrated in FIG. 22. The reliability of an interpolated value is not considered, for example, in the case of a method of performing interpolation by connecting the estimated luminance values of two untested points with a straight line, or a spline method (method of performing interpolation using a polynomial).

Figure 23:
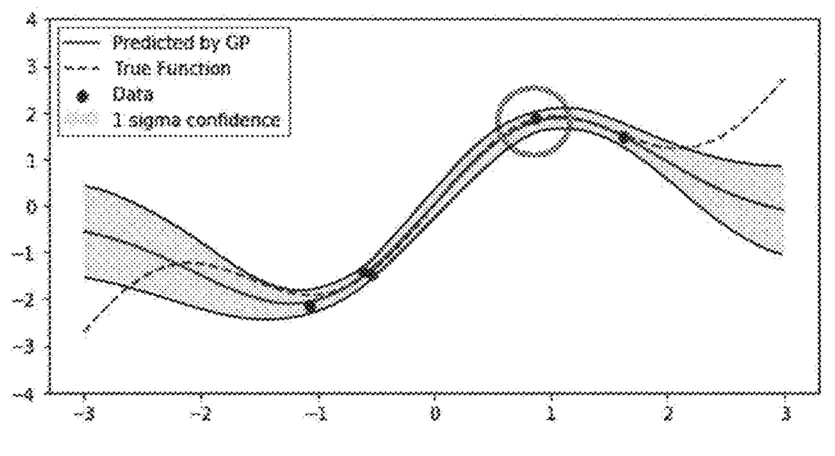
FIG. 23 is a graph illustrating an estimated luminance value and reliability obtained in the present embodiment.

In the present embodiment, the reliability of the estimated luminance value is also estimated together with the estimated luminance value of an untested point. Specifically, in FIG. 23, the horizontal axis represents each test point, and the vertical axis represents the estimated luminance value corresponding to each test point. The dotted line is a line of the correct value, the solid line is a line of the estimated luminance value, and the reliability is indicated as the width centered on the estimated luminance value. Since the reliability is indicated, as illustrated in FIG. 23, an operator can be made to recognize the certainty of the estimated luminance value according to the present embodiment.

In the embodiment described above, the Gaussian process regression is used as the stochastic process, and the Gaussian RBF kernel is used. In the technology of the disclosure, the stochastic process is not limited to the Gaussian process regression. For example, the following polynomial kernel may be used. In the following formula, c is a real number, and p is a positive integer.

$$K(x,x')=(\langle x,x'\rangle+c)^{p} \qquad \text{[Formula 11]}$$

The following Matern kernel may also be used. In the following formula, Kv is a modified Bessel function of the second kind, v is a real number, and Γ(v) is a gamma function.

$$K(x,x')=K_{\nu}(x,x')=\frac{2^{1-\nu}}{\Gamma(\nu)}\left(\frac{\sqrt{2\nu}\,r}{\theta}\right)^{\nu}K_{\nu}\left(\frac{\sqrt{2\nu}\,r}{\theta}\right) \qquad \text{[Formula 12]}$$

$$(r=|x-x'|)$$

In step 136 of FIG. 9 of the present embodiment, the test point setting unit 72 estimates the estimated luminance value of an untested point, and estimates the reliability of the estimated luminance value of the untested point that has been estimated. The technology of the disclosure is not limited thereto. The test point setting unit 72 may calculate a range of possible values of the estimated luminance value of each untested point from the estimated luminance value of each tested point, and calculate a value (for example, a median value) in the calculated range as the estimated luminance value of each untested point.

Each stochastic process described above is the same for each test point of the entire test point set, but the technology of the disclosure is not limited thereto. For example, different stochastic processes may be used in a central area of a predetermined range including the center of the fundus and a peripheral area around the central area.

The untested point of which the estimated luminance value is interpolated is positioned in a range that is reached by indicator light through the pupil of the eye to be tested 12. However, the estimated luminance value may be estimated for a range adjacent to the range that is reached by indicator light, that is, a point at a position that is not reached by indicator light, that is, a visual field test cannot be performed.

In each example described above, a case in which the visual field testing process is realized by a software configuration using a computer has been exemplified, but the technology of the disclosure is not limited thereto. For example, image processing may be executed only by a hardware configuration such as a field-programmable gate array (FPGA) or an application specific integrated circuit (ASIC) instead of the software configuration using a computer. Part of the image processing max be executed by a software configuration, and the remaining processing may be executed by a hardware configuration.

As described above, the technology of the disclosure includes a case in which the visual field testing process is realized by the software configuration using a computer and a case in which the visual field testing process is not realized by the software configuration using a computer, and thus includes the following technology.

First Technology

A visual field testing device including:

a processing unit configured to measure, in a visual field range divided into at least a first partial area and a second partial area, sensitivities of a plurality of first test points that are included in the first partial area; and a test point setting unit configured to perform a process of estimating sensitivities of a plurality of second test points that are included in the first partial area and are test points other than the first test points, by using the sensitivities of the plurality of first test points.

Second Technology

A visual field testing method including:

a processing step of measuring, by a processing unit, in a visual field range divided into at least a first partial area and a second partial area, sensitivities of a plurality of first test points that are included in the first partial area; and an estimation step of performing, by a test point setting unit, a process of estimating sensitivities of a plurality of second test points that are included in the first partial area and are test points other than the first test points, by using the sensitivities of the plurality of first test points.

The following technology is proposed from the above disclosure contents.

Third Technology

A computer program product for performing a visual field test, the computer program product including a computer-readable storage medium that is not itself a transitory signal, the computer-readable storage medium storing a program, and the program causing a computer to execute:

a step of measuring, in a visual field range divided into at least a first partial area and a second partial area, sensitivities of a plurality of first test points that are included in the first partial area; and a step of performing a process of estimating sensitivities of a plurality of second test points that are included in the first partial area and are test points other than the first test points, by using the sensitivities of the plurality of first test points.

The control device 10 is an example of the "computer program product" of the technology of the disclosure.

The visual field testing process described above is merely an example. Therefore, it is needless to say that unnecessary steps may be deleted, new steps may be added, or the processing order may be changed within a range not departing from the gist. Furthermore, the technology disclosed in this specification includes a method of testing an eye to be tested, the method including: a step of presenting light with a plurality of light intensities to a test point set on the retina of the eye to be tested and detecting a sensitivity at the test point of the retina; a step of estimating a sensitivity at a portion other than the test point on the basis of the detected sensitivity at the test point; and a step of evaluating reliability of the estimated sensitivity.

All documents, patent applications, and technical standards described in this specification are incorporated herein by reference as if each individual document, patent application, and technical standard were specifically and individually described to be incorporated by reference.

The disclosure of Japanese Patent Application No. 2021-100268 is incorporated herein by reference in its entirety. Furthermore, all documents, patent applications, and technical standards described in this specification are incorporated herein by reference to the same extent as if each individual document, patent application, and technical standard were specifically and individually described to be incorporated by reference.

The invention claimed is:

1. A visual field testing method, for testing a visual field sensitivity in a visual field range of an eye of a subject, the method comprising:

- a step of presenting indicator light of a plurality of different luminance values to each test point of a plurality of first test points in the visual field range;
- a step of obtaining a measured luminance value at each test point of the first test points by acquiring a recognition signal of the eye of the subject for the indicator light;
- a step of obtaining a calculated luminance value by calculating, from the measured luminance value of each test point of the plurality of first test points, a luminance value estimated to be recognized by the eye of the subject, at a second test point that is a test point other than the first test points; and
- a step of obtaining an estimated luminance value that is a luminance value estimated to be recognized by the eye of the subject at the second test point by obtaining an average value of the calculated luminance value calculated from each test point of the plurality of first test points,
- wherein the calculated luminance value is calculated using a Gaussian process.

2. The visual field testing method according to claim 1, wherein the step of obtaining the estimated luminance value includes calculating an error range of the estimated luminance value.

3. The visual field testing method according to claim 2, wherein the error range is calculated based on a distance between a first test point of the plurality of first test points and the second test point.

4. The visual field testing method according to claim 2, wherein the second test point is an additional test point in a case in which the error range is larger than a predetermined value.

5. The visual field testing method according to claim 1, wherein the step of obtaining the measured luminance value includes determining an upper limit value and a lower limit value of a luminance range of an indicator light to be presented to a first test point of the plurality of first test points in the step of obtaining the measured luminance value, based on a luminance value of an indicator light previously presented to the first test point, and presenting another indicator light of a luminance value within the luminance range to the first test point in the step of obtaining the measured luminance value.

6. The visual field testing method according to claim 5, wherein determining the upper limit value and the lower limit value of the luminance range includes determining the upper limit value and the lower limit value of the luminance range using a cumulative function indicating a relationship between the luminance value of the indicator light previously presented to the first test point and a number of tests.

7. The visual field testing method according to claim 1, wherein the step of obtaining the measured luminance value is performed in the visual field range, the visual field range is divided into a plurality of partial areas, and the step of obtaining the calculated luminance value and the step of obtaining the estimated luminance value are performed in each of the plurality of partial areas.

8. The visual field testing method according to claim 1, wherein a visual field sensitivity map of the visual field range is generated based on respective luminance values of the measured luminance value and the estimated luminance value.

9. The visual field testing method according to claim 7, wherein:

- the division into the plurality of partial areas includes dividing the visual field range into four areas by a horizontal meridian and a vertical meridian,
- a first partial area is an area above the horizontal meridian and on a left side of the vertical meridian,
- a second partial area is an area above the horizontal meridian and on a right side of the vertical meridian,
- a third partial area is an area below the horizontal meridian and on a left side of the vertical meridian,
- a fourth partial area is an area below the horizontal meridian and on a right side of the vertical meridian, and
- the step of obtaining a calculated luminance value and the step of obtaining the estimated luminance value are performed in each of the first partial area, the second partial area, the third partial area, and the fourth partial area, and a visual field sensitivity map of the visual field range is generated based on respective luminance values of the measured luminance value and the estimated luminance value.

10. The visual field testing method according to claim 1, wherein a condition is estimated from the measured luminance value and the estimated luminance value.

11. The visual field testing method according to claim 10, wherein an additional test point is set based on the condition that has been estimated.

12. The visual field testing method according to claim 11, wherein the condition is any of a nasal breakthrough, a nasal step, a temporal wedge defect, an arcuate scotoma, a paracentral scotoma, an altitudinal hemianopsia-like visual field, or a central residual visual field.

13. A non-transitory recording medium storing a visual field testing program that is executable by a computer to perform processing, the processing comprising:

a step of presenting, in a visual field range of an eye of a subject, indicator light of a plurality of different luminance values to each test point of a plurality of first test points in the visual field range;

a step of obtaining a measured luminance value at each test point of the first test points by acquiring a recognition signal from the subject for the indicator light;

a step of obtaining a calculated luminance value by calculating, from the measured luminance value of each test point of the plurality of first test points, a luminance value estimated to be recognized by the eye of the subject, at a second test point that is a test point other than the first test points; and a step of obtaining an estimated luminance value that is a luminance value estimated to be recognized by the eye of the subject, at the second test point by obtaining an average value of the calculated luminance value calculated from each test point of the plurality of first test points, wherein the calculated luminance value is calculated using a Gaussian process.

14. The non-transitory recording medium storing the visual field testing program according to claim 13, wherein the step of obtaining the estimated luminance value includes calculating an error range of the estimated luminance value.

15. The non-transitory recording medium storing the visual field testing program according to claim 14, wherein the error range is calculated based on a distance between a first test point of the plurality of first test points and the second test point.

16. The non-transitory recording medium storing the visual field testing program according to claim 14, wherein the second test point is an additional test point in a case in which the error range is larger than a predetermined value.

17. The non-transitory recording medium storing the visual field testing program according to claim 13, wherein the step of obtaining the measured luminance value includes determining an upper limit value and a lower limit value of a luminance range of an indicator light to be presented to a first test point of the plurality of first test points in the step of obtaining the measured luminance value, based on a luminance value of an indicator light previously presented to the first test point, and presenting another indicator light of a luminance value within the luminance range to the first test point in the step of obtaining the measured luminance value.

18. The non-transitory recording medium storing the visual field testing program according to claim 13, wherein the step of obtaining the measured luminance value is performed in the visual field range, the visual field range is divided into a plurality of partial areas, and the step of obtaining the calculated luminance value and the step of obtaining the estimated luminance value are performed in each of the plurality of partial areas.

19. The non-transitory recording medium storing the visual field testing program according to claim 18, wherein:

the division into the plurality of partial areas includes dividing the visual field range into four areas by a horizontal meridian and a vertical meridian, a first partial area is an area above the horizontal meridian and on a left side of the vertical meridian, a second partial area is an area above the horizontal meridian and on a right side of the vertical meridian, a third partial area is an area below the horizontal meridian and on a left side of the vertical meridian, a fourth partial area is an area below the horizontal meridian and on a right side of the vertical meridian, and the step of obtaining the calculated luminance value and the step of obtaining the estimated luminance value are performed in each of the first partial area, the second partial area, the third partial area, and the fourth partial area, and a visual field sensitivity map of the visual field range is generated based on respective sensitivities of the measured luminance value and the estimated luminance value.

20. The non-transitory recording medium storing the visual field testing program according to claim 13, wherein a condition is estimated from the measured luminance value and the estimated luminance value.

21. A visual field testing device comprising a processor configured to test a visual field sensitivity in a visual field range of an eye of a subject, the processor configured to perform:

a step of presenting indicator light of a plurality of different luminance values to each test point of a plurality of first test points in the visual field range;

a step of obtaining a measured luminance value at each test point of the first test points by acquiring a recognition signal from the subject for the indicator light;

a step of obtaining a calculated luminance value by calculating, from the measured luminance value of each test point of the plurality of first test points, a luminance value estimated to be recognized by the eye of the subject, at a second test point that is a test point other than the first test points; and a step of obtaining an estimated luminance value that is a luminance value estimated to be recognized by the eye of the subject, at the second test point by obtaining an average value of the calculated luminance value calculated from each test point of the plurality of first test points, wherein the calculated luminance value is calculated using a Gaussian process.

* * * * *